(12) United States Patent
Liebman

(10) Patent No.: US 9,744,009 B2
(45) Date of Patent: Aug. 29, 2017

(54) DISPOSABLE MOUTH ARTICULATION SYSTEM

(71) Applicant: Arnold I. Liebman, Brooklyn, NY (US)

(72) Inventor: Arnold I. Liebman, Brooklyn, NY (US)

(*) Notice: Subject to any disclaimer, the term of this patent is extended or adjusted under 35 U.S.C. 154(b) by 0 days.

(21) Appl. No.: 14/615,974

(22) Filed: Feb. 6, 2015

(65) Prior Publication Data
US 2015/0305838 A1    Oct. 29, 2015

Related U.S. Application Data

(63) Continuation-in-part of application No. 13/905,642, filed on May 30, 2013, now Pat. No. 9,545,294.

(51) Int. Cl.
A61C 9/00 (2006.01)
A61C 13/34 (2006.01)
A61C 11/08 (2006.01)

(52) U.S. Cl.
CPC ............ A61C 9/0006 (2013.01); A61C 9/002 (2013.01); A61C 11/088 (2013.01); A61C 13/34 (2013.01)

(58) Field of Classification Search
CPC ..... A61C 9/0006; A61C 9/002; A61C 11/088; A61C 13/34

USPC ............................................. 433/37
See application file for complete search history.

(56) References Cited

U.S. PATENT DOCUMENTS

| | | | | |
|---|---|---|---|---|
| 3,577,855 A * | 5/1971 | Baum | .................. | A61C 19/045 33/514 |
| 3,890,711 A * | 6/1975 | Burns | .................. | A61C 9/0006 433/41 |
| 4,838,789 A * | 6/1989 | Tanaka | ................ | A61C 13/0001 433/171 |
| 8,277,216 B2 * | 10/2012 | Kim | ..................... | A61C 9/0006 433/37 |
| 8,360,772 B1 * | 1/2013 | McCarthy | ............ | A61C 9/0006 433/41 |

* cited by examiner

Primary Examiner — Cris L Rodriguez
Assistant Examiner — Mirayda A Aponte
(74) Attorney, Agent, or Firm — Andrew S. Langsam; Pryor Cashman LLP

(57) ABSTRACT

System, components and method for creating a set of dentures using the patient's mouth as an intra-oral articulator by use of an upper and/or lower disposable dental impression tray for creating the impression of the edentulous or partial edentulous mouth, the trays having a horizontal support bar and an upwardly extending short wall, with ridges, for mechanically accepting waxed backs of artificial teeth thereto. A screw with partial palatal tray can be secured through an aperture of the horizontal support bar and locked in place.

8 Claims, 17 Drawing Sheets

SECTION B-B

SECTION A-A

US 9,744,009 B2

DISPOSABLE MOUTH ARTICULATION SYSTEM

RELATED APPLICATIONS

The present invention is a Continuation-in-Part Application of application Ser. No. 13/905,642 filed May 30, 2013, to which priority is claimed and which is incorporated by reference herein.

FIELD OF THE INVENTION

The present invention relates to a system and individual components for use by a dentist to facilitate the creation of a model of the interior of a patient's mouth, one or more teeth therein, the gums, palatal arch, etc. for use with forming suitable and aesthetic pleasing and attractive replacements for one or more teeth for a dental patient. Specifically, the present invention discloses an intra-mouth articulation device, a system and disposable components capable and intended for use for the individual patient to facilitate the creation of artificial teeth, bridges, entire uppers and/or lowers, and teeth structures, etc. and more specifically relates to an integrated dental system, components and a method for forming dentures, partial dentures, individual implants and related teeth all in the aid of dental procedures and products. The present invention discloses a new device and associated components for use by a dentist within an individual's mouth to provide an intra-oral, disposable dental articulator for use in forming dental impressions and an individual or sets of teeth for a partial or complete set of dentures.

BACKGROUND OF THE INVENTION AND DESCRIPTION OF SYSTEM, COMPONENTS AND METHOD OF USE

As many individuals age they can become partially or completely edentulous, i.e., they lose one or more teeth and, yet, gum tissue remains. This can be caused by a wide array of issues, including periodontal disease, tooth decay, improper nutrition, simple decay, developmental defects, genetic defects, and/or or trauma or other factors, presenting alone or in combination. When this occurs, individuals lose some or all of their teeth and should be fitted with one or more replacement teeth or a complete set of false teeth or bridges, implants, partial or full dentures, etc. (hereinafter often collectively referred to as "dentures," but it should be understood that the term is meant to be inclusive of everything and anything which a dentist may select to remediate a patient's mouth including one tooth or one or more teeth, i.e., within the normal range of dentistry), to replace those having been decayed, lost over time, disfigured and meant to be replaced, etc. To remediate and provide one tooth or one or more new or replacement teeth, patients or individuals in need often get dentures, which are prosthetic, false (often acrylic or more expensive porcelain) teeth constructed to replace the tooth or, more likely, more than one tooth, hereinafter for ease of illustration referred to as "teeth." Removable, whether a single tooth, a bridge, multiple new artificial teeth, etc. are referred to herein as the representative illustration as full or partial dentures and are used when an individual has lost only some teeth and/or a complete set of dentures, or dental implants, can be used when an individual is substantially or fully edentulous. Providing a full or partial set of dentures to an edendulous patient is the illustrated embodiment but those of ordinary skill in the art will readily appreciate that the systems and components of the present disclosed invention can be adapted for many dental procedures without departing from the basics taught herein.

The process, in the past, is done by a qualified and licensed dental practitioner and often requires more than a single dental appointment for first taking appropriate molds of the patient's upper and lower arches and gum topography, then sending the same to a lab, having the lab create proposed new teeth and then fitting the same into the patient's mouth. This is time consuming, expensive, possibly embarrassing to the patient until the dentures are provided, inconvenient to the patient, and often results in compromising the quality of the end product. It is believed that a one-time, possibly single visit to the dentist's office, which will allow a fully or partially edentulous patient to go from a state of edentulousness to beautiful smile with a partial or complete set of teeth or dentures, would be a huge boon to the patient, to the dentist, and to the dental manufacturer supplying the various components. This would likely be exceptionally advantageous to otherwise poorly served communities where the number of dentists is small and the ability to pay is lacking, too, by the patients.

The present invention discloses the individual disposable components, an integrated system, and a comprehensive method for preparing a set of dentures—partial or full, uppers and/or lowers—possibly in a single visit by using the patient's own mouth as the holding chamber or cavity for the molds and teeth to be used in the formation of the dentures. In effect, the present invention provides an easy to use, inexpensive, disposable device(s) for allowing the patient's own oral cavity to serve as the articulator for preparation of the dentures. Stated differently, by providing a new integrated component and a device, along with proposed and artificial teeth (or single tooth) including a set of trays which are used within the patient's mouth for forming a mold of the gum lines and teeth which can be secured to the trays, dentures can be fitted, in color, size, type, bite, fit, etc. and made to fit in preferably a single visit to the dentist. Additionally, the components for the articulation system are meant to be disposable and thus inexpensive to produce. No sterlilyzing or autoclaving between patient visits is contemplated by the present invention. Rather, the trays and teeth attached to the trays are used for that patient, the completed representative new set of dentures then turned into proper dentures, and the trays, the teeth then discarded and a new set of the present components used for the next patient. The cost savings, time savings, comfort to the patient, the dentist's profitability, etc. will likely all be maximized. This is a primary goal of the present invention.

Finished dentures are preferably composite or acrylic-molded teeth fit which are integrated into an acrylic set of gums which, as a unit, uppers and lowers, are then adhered or form fit into the mouth of a patient, fitting and being secured on the remaining gums of the patient. These replacement teeth will be located where the patient's original teeth have been lost, removed or destroyed. The gums of the patient serve to hold the new acrylic gums of the dentures and they hold the new and attractive, in color, size, shape and fit, teeth of the patient. The patient will insert the new dentures into the mouth with the female concavity of the new gum of the denture fitting over and precisely accepting the remaining male or upwardly protruding gum(s) of the patient's mouth. The new acrylic or porcelain teeth will project out through the patient's mouth in a pleasing and useful manner. Of course, the new teeth are meant to match the patient's original teeth or to provide an enhanced set of teeth, all to provide a suitable and pleasing smile with suitably shaped and colored teeth for the patient's mouth, complexion, smile lines, etc. For purposes of this disclosure, all types of dental procedures made possible by the present invention, namely full dentures, partial dentures, single or multiple teeth, bridges, new dental implants, dental implant retention, and other procedures, will often be hereinafter referred to collectively as "dentures."

A system, set of components and method for creating a set of dentures for a patient by using the patient's mouth as the articulator (where in the past, except for my own prior invention which this invention is a continuation in part a separate mechanical articulator was used) is presented, comprising customized disposable lower and upper dental trays for first creating an impression of the patient's lower ridge and upper ridge or remaining gums of the mouth, respectively, a customized upper and lower palatal dental tray for creating an impression of the patient's upper and lower mouth portion, respectively, including the palatal arch, and a means to lock the same in place for accurate separation and spacing of the impressions formed in the upper and lower trays while also serving as an artificial tooth holding device. Basically, the present invention allows the dentist to use the patient's own mouth as the cavity and vehicle within which to create the set of dentures. This is accomplished by providing a set of disposable trays for creating dental impressions of the holding gum ridges and then securing to the new trays the color, shape, size, etc. teeth, which then allow a complete set of dentures to be formed for ultimate placement in the patient's mouth.

The disposable trays of the present invention allow for vertical adjustment of the spacing between the impressions formed by the disposable trays while within the patient's mouth and for locking the same into place—that is, for proper distance from one another which is important in replicating the spacing when the final dentures are created—all while the trays are within the patient's mouth. The patient and dentist thus are provided with the precise color, shape, type, location, fit of the proposed teeth within the patient's mouth and are not forced to use a separate mechanical articulator to try to envision the dentures in the mouth. Clearly, not onlyure speed, expense are saved, but the end product is likely to be far better in fit, look, comfort, color, etc. to both dentist and patient as the dentures are seen in the actual mouth of the patient during the procedure.

The disposable trays coordinate with other associated components, allowing dental impressions of the gum ridges, palatal arch, and remaining teeth of the patient's mouth to be obtained. According to the invention, new and inventive lower and upper impression-forming trays are each provided with a set of concave platforms which are configured to fit around the gum ridges or existing teeth (in the case of a partially edentulous patient). Those aspects of the trays are similar to current trays used for making upper and lower dental impressions. Suitable impression material is placed into the channels, they are fit over the gum ridges and/or teeth and the material quickly cures to form a female impression of the gum ridges, the palatal arch and the remaining teeth. The dentist can quickly "pop" the impression material off of and out of the mouth after curing and then the impression is useful in making a corresponding male version of the dental structure (corresponding to the actual mouth of the patient) and from that the end denture gum-holding structure can be formed. The disposable trays of the present invention, however, are new and distinct in that in addition to providing a suitable means to create the female of the gums for fitting over the remaining gums of the patient (the female gums to hold the new teeth of the dentures) the trays provide surfaces for selective attachment of new artificial teeth which can then be molded to the impression material, all toward the goal of creating a new set of denture, teeth and gum holding components, all while allowing the dentist to place the teeth on the trays to "see" the teeth, in color, size, shape, fit, etc. within the patient's mouth. Then, with the complete trays and teeth assembled within the mouth (in effect the patient's own mouth is the substitute for the otherwise separate mechanical articulator for the creation of new dentures) the dentist can either create the dentures then or send the entire "build up" to the lab for creating porcelain or acrylic teeth/dentures. Those will have the gum securing impression and the final color, shape, placement, fit, etc. of teeth.

The trays are held in place within the mouth by the channel being superimposed over the remaining gum line or ridge. The tray is used for both creating the gum ridge holding impression and for placement of the teeth in the mouth for fitting of the teeth. A vertically adjustable screw with a palatal shaped cap is provided which enables the securement of the lower tray within the mouth and serves as a palatal arch component. The cap is secured to the top of the screw head and not only positions the lower tray from the upper arch for use by the dentist when the tray is removed from the mouth but also serves to easily allow the distance to be comfortably and accurately maintained as the palatal arch of the screw's cap can be locked in position, as desired during the process. The palatal tray member can be vertically positioned in the mouth with respect to the lower tray to match the vertical distance between the top and bottom of a patient's mouth.

One or more sets of teeth or units of dentures comprised of a wax substrate and the actual and appropriate color, size and shape of tooth (teeth) sought to be created for the patient is also provided by the present system. These units are securable to the tray while within the patient's mouth by adding wax to the rear of the sections of artificial teeth and pressing the wax on the back of the artificial teeth to a vertical set of ridges or grooves which extend convexly around the tray. The grooves basically follow the curvature of the mouth and extend vertically. The rear of the artificial teeth, with wax thereon, can be press fit to and against the forwardly projecting vertically ridges or grooves to adhere the teeth with wax to the front of the tray. This will allow the patient and the dentist to see how the teeth will look, within the patient's mouth, so that changes can be made, in color, size, shape, fit, etc. while using the patient's mouth as the mechanical articulator. Then, once the teeth on the tray is established as suitable and proper, the tray with teeth can be removed and the final dentures created either by using the same artificial teeth along with a new gum impression or by sending the fulfilled system to the dental lab. Then, the teeth with the proper fitting, gum female component, for fitting over the remaining gums of the patient, can be made. The patient is thus provided with a new set of dentures.

The position of the units of teeth can be adjusted with relation to one another, to the gums, lips, mouth other anatomical components (lower lobes of ears and beneath the nose line, etc.) for appropriate fit, look, and placement.

Once properly set up, with the gum holding impression and the new artificial teeth secured to the disposable tray, the dentist can either use the resultant product to create in his own lab a set of dentures or send the same to a lab for the same. An external articulator can be used to complete the process since the relative orientation of the trays and the teeth are then fixed, all with respect to one another and as set by and within the patient's own mouth. The present invention allows for creation of an accurate set of dentures, using the patient's mouth as the articulator, providing a system and method to do so in a single visit, thereby minimizing the time required for this process, and utilizing inexpensive, disposable components for a relatively low-cost procedure.

Basically, to prepare a set of dentures using the present invention, the disposable tray (upper or lower) is placed in the patient's mouth for impressions to be taken of the upper or lower remaining gum configurations. They, of course, will support and hold the new dentures. The impressions will be used to create the new dentures with the teeth embedded or secured therein.

The mouth can be held open, if needed, using a set of retractors to pull the lips and cheeks apart, and providing free access to the gums. To make and take each impression, a customized upper or lower tray are provided which is first filled with soft, quickly curable, dental impression material. The impression material is preferably made of a flexible, formable material, capable of being cured and shaped in the exact configuration of the gum ridge formed and found in the bottom and top of the edentulous patient (for purposes of ease of illustration a complete edentulous mouth is considered herein, but the same procedure can be utilized for a partially edentulous patient).

Once the impression material is placed in each tray, the trays can be placed, preferably one at a time, into the mouth of a patient, on the upper and lower gums, respectively. The trays having holding handles, either integrated with the trays or removable therefrom when the trays are used for following steps. The trays are generally similar to current trays used for creating impressions of a patient's mouth, i.e., a semi-circular trough which will fit over, with impression material first placed therein, the gum ridge and teeth, if any, of the patient. Over a short time, the impression material hardens and the tray then removed. The resulting female cavity is the negative for forming an a new denture which will fit over and be secured and located on the gum ridge of the patient, just as is done in current procedures.

The impression material will cure or harden (by mere passage of time, by a light curing device, etc.) once in place in the tray and within the mouth, thereby creating a female or negative mold of the gums of the patient's mouth. In the preferred embodiment, the trays are coated with polyvinyl siloxane (hereinafter "PVS") for quickly and easily forming the impressions of the upper and lower gums. A suitable tray is used, much as in conventional dental molding or impression formation, with the proper shape, size, upper or lower, of course, being taken into consideration. However, according to the preferred embodiment of the invention, the impression forming trays are modified from that conventionally available for impressions as they are not only disposable, but provided with a vertical screw mechanism to measure the distance between the gum line and the roof of the mouth for accurate impressions for the artificial teeth to be formed by the present invention. And, importantly, as mentioned, illustrated and described, these new trays have semi-circular, vertically extending holding ridges which allow new artificial teeth, back waxed, to grip thereto for positioning and placement within the patient's mouth. This allows adjustment to the positioning, color, size, shape ad fit of the artificial teeth within the patient's own mouth, before creating the final dentures. Using the patient's own mouth as a substitute for the mechanical, separate articulator is believed to be a huge new advantage in the denture field.

The upper and lower trays, consistent with the present invention, are preferably used and provided with an easily snappable, removably-coupled small, forwardly protruding handle, which allows the dentist to place the tray into the mouth and remove the same after the impression material cures. The handle allows the dentist to control and direct the tray(s) into the desired location in the patient's mouth and, yet, is easily removed from the tray, after the tray, with the impression material cured, is removed from the mouth. The handle allows a dentist to properly position the trays into the mouth along the upper and lower gums and hold them in place so that the impression material can cure and harden. The removable handle allows the cured impression and the tray to be easily removed from the patient's mouth. Also, after the mold is created for the gum-holding component of the dentures, the tray is inserted and removed for the placement of the new artificial teeth thereon. The handle facilitates this entire effort.

Prior to the impressions or molds being taken, the vertical dimension of occlusion (the distance between the two dental arches) can be measured and recorded by the dentist, as is conventional. This procedure can be done according to conventional dental or industry standards—i.e., a pen dot is placed on the patient's tip of the nose and center of the chin, the patient relaxes by breathing in and out with their lips closed, and once relaxed, a ruler is used to measure the dot of the nose-to-chin distance, i.e., from one dot to the other. Additionally, the upper tray is preferably provided with a cross bar and an internally threaded aperture in the center thereof. A corresponding and mating screw with a cap as a palatal arch is provided. The screw threads are received by the threads of the aperture and the screw, with the palatal arch bearing up and against the bottom of the patient's palatal, adjusted so that the distance between palatal arch of the patient and the gum ridge at the bottom of the patient's mouth measured and locked in place. A locking ring will hold the screw in place and the entire system, tray and screw with palatal arch and locking ring, can be removed and replaced as desired and needed into the patient's mouth. The free end of the screw is inserted into the threaded aperture of the cross bar of the lower tray by mechanical locking of the external screw threads of the screw and the internal screw threads of the aperture. The palatal arch or cap of the screw is then moved up and down so that it precisely touches the actual palatal arch of the patient. Then, the locking nut is tightened. This allows the dimension of occlusion to be measured and maintained even as the trays are removed and then reinserted in place, i.e., within the mouth, to be held in place while the artificial teeth are attached to the tray and even while the completed systems is then used to create a set of dentures. Each tray preferably comprises a mold forming component (like a trough in semi-circular shape corresponding to shape and size of the patient) which overlies the corresponding gum line.

The palatal piece secured to the top or cap of the screw head is preferably smaller than the full trays as it is not designed to create a mold of the upper gums for teeth, but merely to rest below the roof of the mouth so as to provide proper measurement of the vertical opening of the mouth while either tray is placed therein. The small palatal arch is a substitute for a full upper molding tray and is believed more comfortable in use. During initial use, the vertical dimension of the palatal tray can be moved relative to that of the lower tray to which it is secured, all to match the height, space, orientation, and angle of the interior cavity of the patient's mouth all while within the patient's mouth.

A separate palatal tray, similar to the lower tray is provided. Additional impression material can be placed into the palatal tray so as to get an additional negative mold of the upper arch and upper gum ridge of the mouth as well. This can be used later, as will the impression formed by the lower tray, to create stone molds of the patient's mouth and then custom trays, to be used with the upper and lower trays and the artificial teeth, all to create dentures for the patient.

When the lower tray is removed from the patient's mouth having a cured mold impression of the gum ridge therein and with or without the palatal tray connected thereto (via the screw) a negative mold created in the tray should allow the tray to be reinserted into the patient's mouth and to sit comfortably on the gum ridges (after all, the mold matches that of the patient's gums) thereby allowing the palatal tray to move into place into the roof of the mouth in accordance with the curvature and location of the upper arch of the mouth while the lower impression fits over the lower gum ridge. Once the lower tray and palatal tray are located within the mouth, and height and relative side, forward, occlusion dimensions satisfied, the dentist can "lock" in place the height of the screw with the palatal tray using a locking nut which mates with the screw, and thereby lock in place the relative location and orientation of the lower tray and its impression material and the palatal tray. Upon securement of the height of the screw and palatal tray in place in the aperture of the cross bar of the lower tray, the tray can be removed from the patient's mouth. Basically, the same procedure can be used for impression of the upper gum line.

To ensure proper placement of trays within the mouth and to ensure teeth orientation vis a vis the patient's mouth, lips, ears, nose, etc., an occlusal plane device is provided and can be used. This device is a thin, flat, semi-circular or arc shaped accessory, which connects to the lower tray and will extend outwardly and surround the separation of the patient's lips. In the present invention, the occlusal plane accessory or device is also made of a disposable material so that it may be used for a single patient and then disposed of after completion of the dentures. This device allows the dentist to ensure dental principals are maintained, i.e., for example, relative horizontal location of the lower tray across the patient's face, facilitating alignment of the nose, the lower ends of the ears, the patient's eyes, ensuring proper location of the tray and the proposed artificial teeth across the patient's face. The occlusal plane device is positioned to help the dentist align the teeth substantially parallel to the eyes, nose, and the ala tragus of the patient, ensuring that the tray(s) and the artificial teeth secured thereto are placed in the proper alignment so that the installed dentures will be straight, as desired, and not crooked or misaligned with the patient's face, mouth and lis. This is all done consistent with standard dental principles.

Teeth can then be secured and held to the trays. Dental wax can be secured to the rear of a set of acrylic or porcelain teeth, which can then be pressed against and thus frictionally attached to forwardly projecting ridges or vertical grooves of the upper and/or lower tray for holding and maintaining the artificial teeth in place thereon. These artificial teeth are selected by color, size, shape, fit, etc. from available artificial teeth, all maintained by the dentist for this procedure. One or more teeth may be provided for this purpose but the dentist, selecting the proper teeth will push the rear waxy surface of the teeth against the vertical ridges of the trays to hold the same in place. In this manner, the dentist is creating a new set of artificial teeth, using the patient's own mouth as the mechanical articulator, for the purpose of creating a new set of dentures.

This allows a dentist to position the teeth in proper size, spacing, color, fit, location, etc. with respect to one another and within the mouth and with reference to the gums, lips, and nose of the patient—allowing the dentist to replace, adjust and move the artificial teeth on the tray until the exact set of new artificial teeth is visible. In one embodiment, the wax will then cure or harden and set so that the dentist can remove the same and create the actual set of dentures. In one embodiment of the present invention, the used artificial teeth are the final end product artificial teeth of the dentures. In another embodiment, the artificial teeth used by the dentist for the purpose of creating the new "look" and set of teeth are used by the dentist or the lab to create a new set of dentures, acrylic or porcelain.

In one embodiment, the teeth are assembled and adjusted within the patient's mouth. Ina another embodiment, the teeth are assembled in a mechanical articulator but the trays are used to insert and "try" the trays and teeth into the patient, as desired.

The upper and lower negative impressions of the gum and mouth structure—as taken by the upper tray, lower tray, and palatal tray—can be poured with dental stone. The dental stone creates a positive impression of the patient's mouth, as it will form within and around the negative impression made by the molded and then cured impression material in the trays.

A standard, mechanical, external-to-the-mouth dental articulator can be used as a holding unit for the stone models. Quick setting dental plaster can then be placed on the bottom and the top of the conventional articulator; the stone models just formed being still attached to the trays, holding it until the quick-set plaster is dry. Once the stone models are made, either tray can be placed between the models so that the proper height of the overall stone model, i.e., the distance between the top of the palatal tray and the bottom of the lower tray, can be determined. Quick setting dental plaster can then be poured on top of the upper stone model to fill in the gap between the top of the upper stone model and the top of the conventional articulator. This serves to hold all pieces in place at the correct distances corresponding to that of the patient's mouth as determined by the patient's upper and lower gums, their separation, all as replicated by the use of the trays and their impressions, as adjusted. If the configuration of the trays with molded impression material matches the stone models exactly, a perfect reconstruction of the mouth has been made and with the new dentures visible. This will facilitate the construction of the dentures. This procedure with the mechanical articulator can be done separately for the lower tray with upper palatal tray connected thereto and for the upper tray with lower tray connected thereto. Thus, a stone model can be taken of the trays with impression material and of the palatal tray to match the cavity and curvature of the interior of the patient's mouth and to accurately measure the distance between the top and bottom of the mouth.

After the stone models are complete, the impression material can be removed from the trays and the stone models. Light-cured material can be placed over the upper and lower stone models—which are now positive replicas of the patient's mouth—and maneuvered into place to form custom impression-like trays (hereinafter referred to as the "custom trays") of the top and bottom of the mouth, in the same manner that the original impression material was used. When heated with light or otherwise cured, the custom trays will be set in place and form negatives of the patient's mouth, adapted to fit perfectly onto the stone models and thus into the patient's mouth itself. The custom trays can be placed onto and into the stone models and placed back into the conventional articulator and/or into the patient's mouth, adjacent to the lower tray and upper palatal tray.

The dental wax added to the rear of the new artificial teeth serves to hold the teeth in relative orientation with respect to the other adjacent teeth in the same row (upper and lower) in the unit and with respect to upper and lower teeth of the same unit. The wax serves, at least temporarily, as the gums into and onto which the patient's teeth will be held and located. The back-waxed teeth can then be placed onto the exterior surface of the tray (pressing the same against the vertical ridges) so that the teeth may be set in place relative to the tray for proper positioning.

Once the custom trays are re-connected to the stone models in the conventional articulator, commercially available baseplate dental wax can be heated up and attached to the custom trays to connect the impressions of the custom trays (upper and lower) to the wax substrate attached to the units or sets of teeth adhered to the exterior surface of the trays so as to leave no interstitial tooth to adjacent tooth gaps. This dental baseplate wax will also become malleable once heated, and it is adapted to be inserted along any ridges or troughs in the custom trays and to seal together the teeth to the respective upper and lower trays. The combination of wax and the teeth units, with the custom trays, will create a positive mold of the gums of the patient so as to perfectly match that patient's mouth. This will provide a dentist with the correct height and depth of the dentures so the teeth are properly positioned and orientated. This step will be performed for both the lower and upper custom impression trays.

When the base-plate wax has cooled and become set into place, the units or sets of teeth are be connected by baseplate wax to the custom trays. This will leave an upper mouth impression and a lower mouth impression, each made of the stone model, impression of the custom tray, base-plate wax, and teeth sets.

Once the stone model and wax molding is complete, conventional dental lab work can be provided, either on site at the dental office, or sent to a stand-alone dental lab. The custom trays can be turned into a final set of dentures, using basic dental principles. The same acrylic teeth of the teeth units used and adjusted on the tray can be used for the final set of dentures for a patient, with the wax molding of the custom trays (resembling the gums) replaced with acrylic. Using the technique disclosed herein, a set of dentures can be made with a perfectly molded set of "gums" which match the orientation, angle, curvature, and shape of the particular patient's mouth, so that the dentures will fit the mouth as if they were the patients' actual teeth. Additionally, the entire system and method described above can preferably be completed in a single visit, and preferably using all inexpensive disposable components.

It is an important aspect of the present invention that the units and teeth of the units used herein can actually be the final teeth of the dentures ultimately provided to the patient for use.

The products disclosed herein and the disposable system are prepared to accept digital conversion. More specifically, the present invention can be integrated to perform as a digital mouth articulator system. Thus, the devices, methods, and system can compete with digital denture companies, which are currently lacking in anterior teeth setup.

The present invention is also fully intended to be integrated with currently available and expected to be available scanning technologies, too.

The entire product and its tooth (teeth) secured to the rib of the in-mouth dental articulator can be stored and used as a CAD file. When used with existing and to be developed dental scanning technologies it will provide additional data points for implant planning software for measurements and implant planning.

Denture teeth that have known CAD data can also be placed onto the tooth rib and used with scanning technologies. This also provides much more data than currently possible.

A practitioner or a dental laboratory can elect to place identification markers or measurement markers onto or embed into the tooth rib or other component of the IntraOral Articulation System or device with scanning technologies for additional data for measurement information and implant placement information.

This and other aspects of the present invention are disclosed herein. The present invention comprises a set of new dental components, a new system and a new method for forming a set of dentures, primarily by using the patient's mouth as the intra-oral articulator. The present invention comprises new upper and lower impression forming trays with a mechanism for holding thereon a single or set of artificial teeth by use of wax on the rear of the new and artificial teeth which will grip and be held to a set of ridges on the forwardly projecting semi-circular set of ridges of the trays.

DESCRIPTION OF PRIOR ART

Currently, to create and make a set of dentures, only conventional mechanical articulators outside of the mouth are used. This can create errors in the color, size, placement, shape, look, measurement, angulation, occlusion, and placement of dentures if they do not precisely match the shape of the mouth and face once placed therein. The present invention aims to overcome these issues by presenting new components and a new system and method for creating a set of dentures using the patient's own mouth as the mechanical articulator, rather than reliance solely upon an external mechanical mouth replicating device. By using the patient's own mouth as the placement of proposed artificial teeth, a far more accurate set of dentures, in a small amount of time, is provided. There is also a need for a set of dentures which can accurately be created for a patient in a quick, relatively inexpensive, and easy fashion, as opposed to a process which requires multiple dental office visits to complete. The present invention provides an accurate and quick system and method for making dentures using inexpensive and disposable components for the articulation system within the patient's actual mouth, all of which are inexpensive and easy to produce.

SUMMARY OF THE INVENTION

The present invention discloses components, systems, and methods for creating a set of dentures by using the patient's mouth as an intra-oral articulator by use of an upper and/or lower dental impression tray for creating the impression of the edentulous mouth, the trays having typical semi-circular channels or troughs which allow for accurate impression of the upper and lower gum lines and a semi-circular set of vertical ridges for providing a frictional backing connection to a set of wax-based artificial teeth for creation of a set of dentures. A screw with a cap is provided, too, as a palatal tray. The cap is secured to the head of the screw and it threads into an aperture in the cross member of the lower tray. The distance of the cap to the base tray's cross member is adjustable by threading the screw into the aperture of the cross member and, when adjusted, the distance can be locked in place. Artificial teeth formed with holding wax on their rear surfaces can be secured to the semi-circular ridges of the impression trays while located within the patient's mouth to accurately locate the same in place. The wax holding the artificial teeth is then melted to integrate the teeth with the gum lines which were previously obtained from the upper and lower trays.

The present invention incorporates by reference the Figures and related description of applicant's co-pending and priority US Patent Application and specifically those drawings and description relating to FIGS. 9, 11a-11g, 15a-15e, 17a-17e, 18 and 19.

Figure 11A:
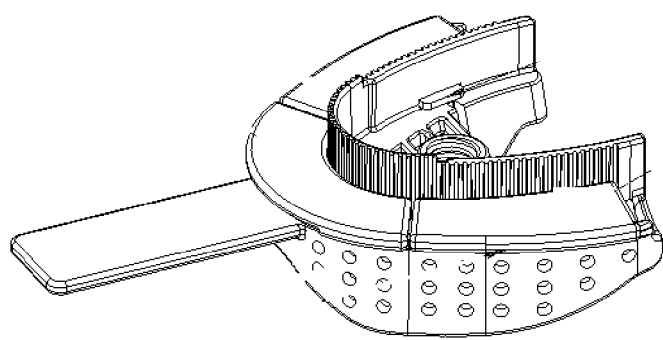
Figure 11B:
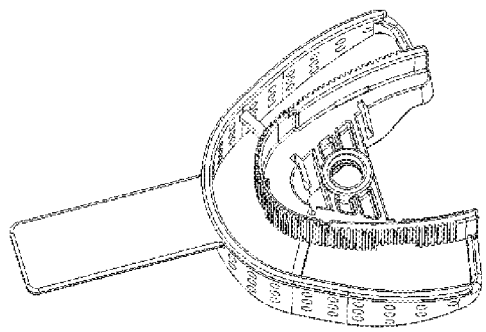
Figure 11C:
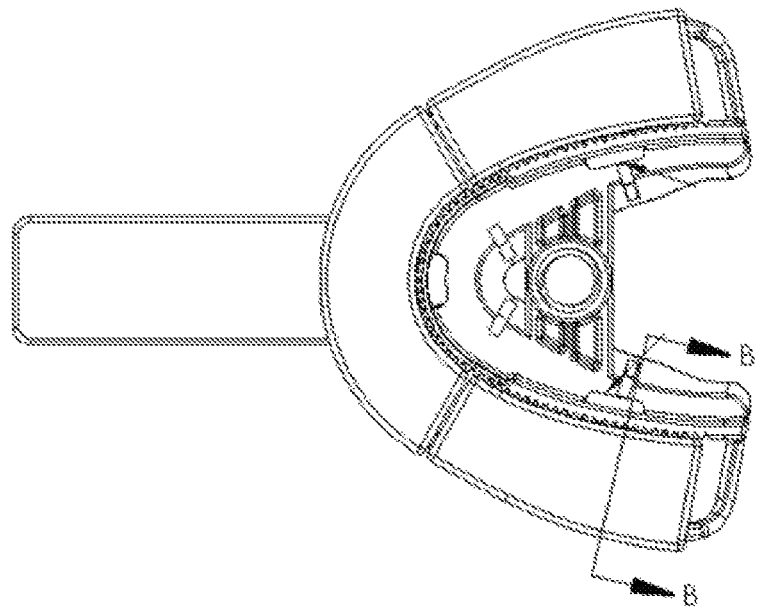

FIG. 11a is a perspective view of the lower tray for partially edentulous patient use and shows the use of three separate covers overlying the impression channel;

FIG. 11b is a similar but 180 degree rotated view of the tray of FIG. 11a but showing the devicer without the covers thereon;

FIG. 11c is a top plan view of the lower tray with covers thereon; and

Figure 11D:
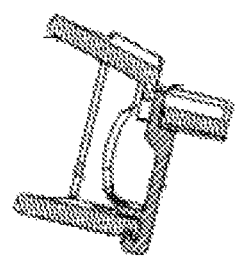

FIG. 11d is a cross sectional view of the lower tray of FIGS. 11a, 11b, and 11c, taken along the lines B-B of FIG. 11c and shows the tabs and hooks holding the covers in place and further shows how the tabs and hooks, with the rib 11 to the underside of the tabs opposeds the hooks and prevents the tabs from inadvertently releasing.

Figure 12:
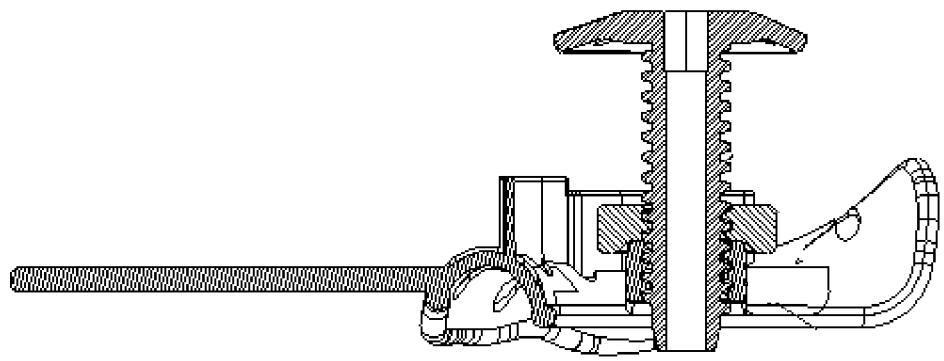
Figure 13:
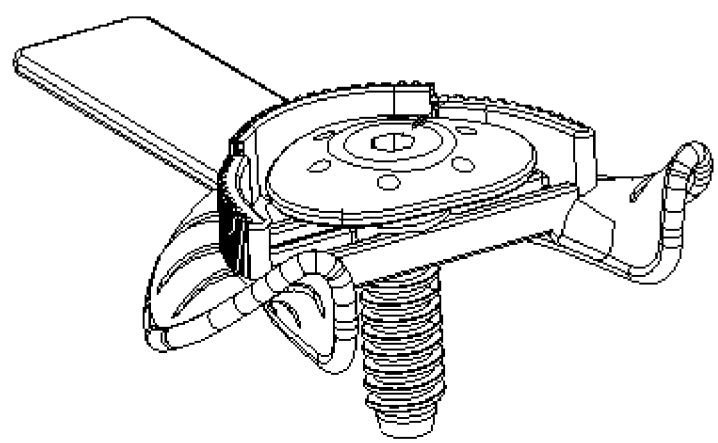
Figure 14:
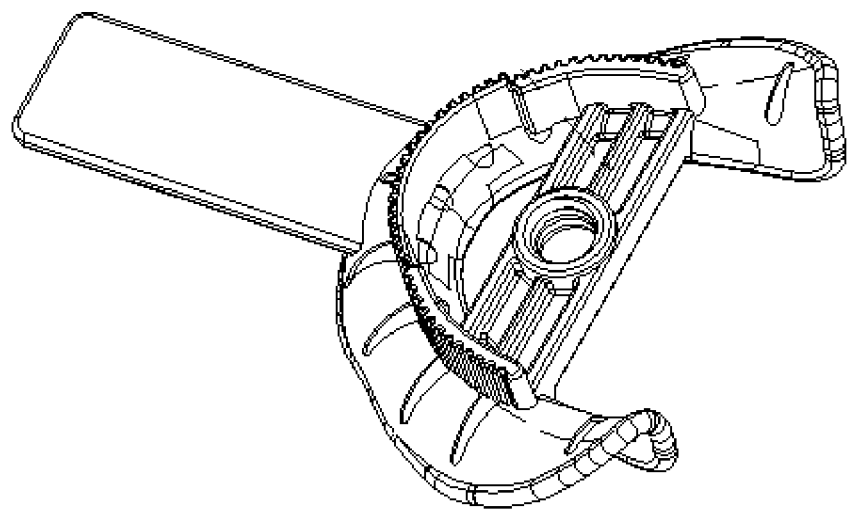
Figure 15:
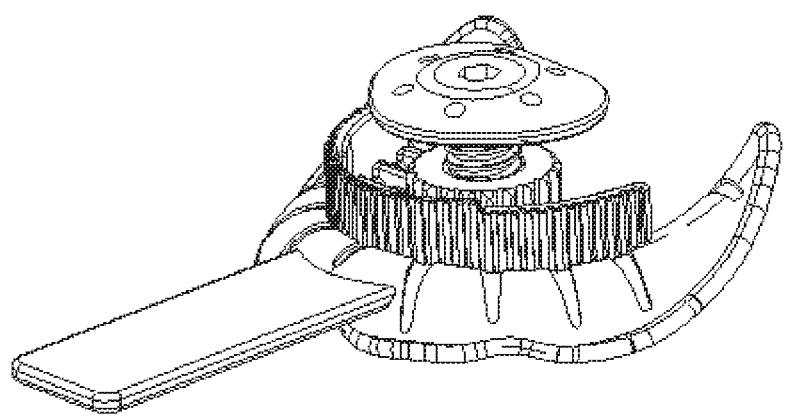
Figure 16:
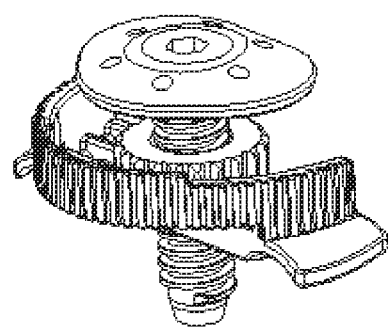
Figure 17:
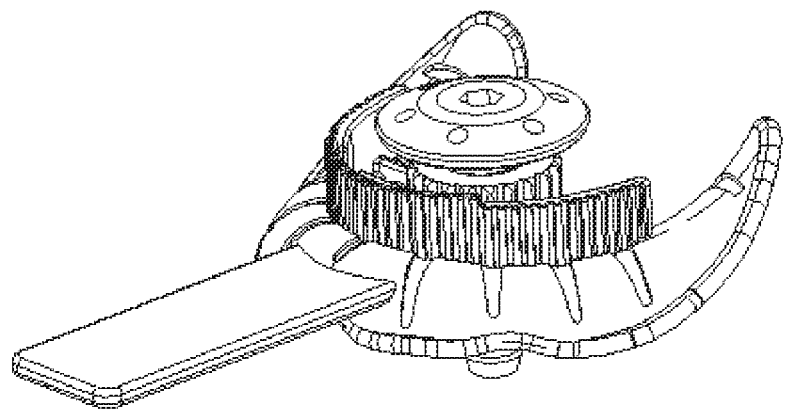
Figure 18:
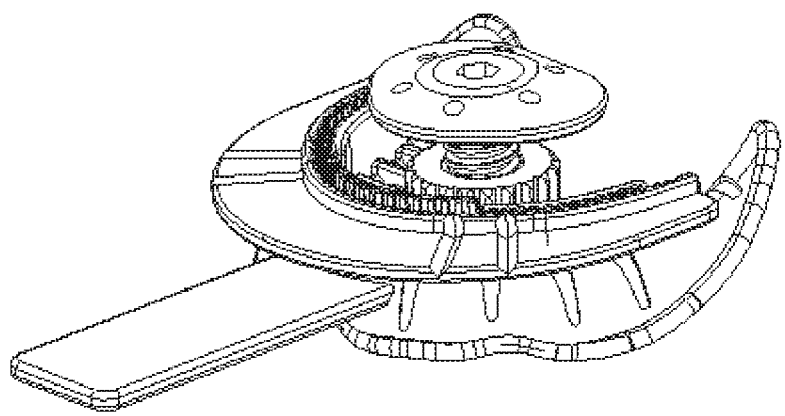
Figure 19:
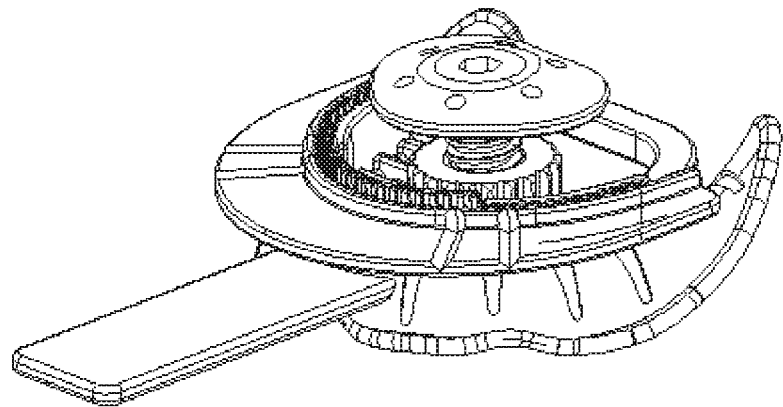
Figure 20:
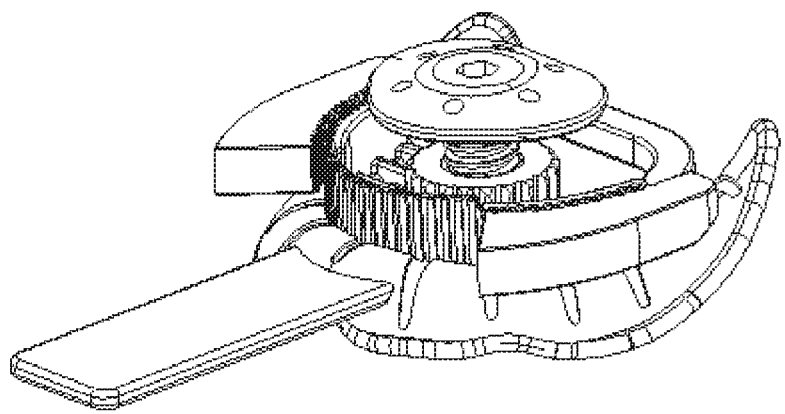
Figure 21:
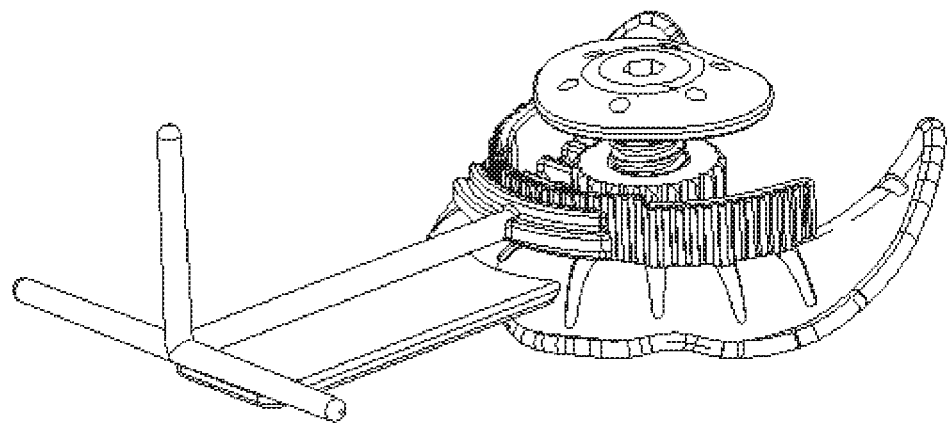
Figure 22:
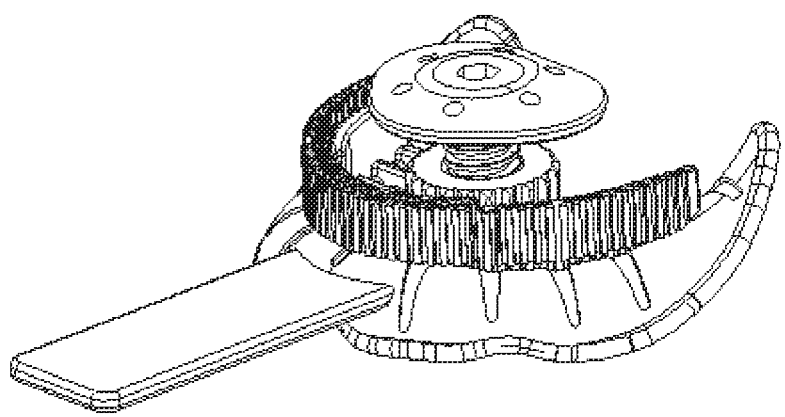

FIG. 12 is a cross sectional view of the lower tray with the palatal screw, with its palatal or cap, held by a jam nut within the aperture of the lower tray and with the handle for the lower tray extending out of a patient's mouth to facilitate entry and removal therefrom;

FIG. 13 is rear perspective view of the lower tray, with handle projecting out of the patient's mouth and shows the position of the screw with its cap, the threads being received by the aperture of the horizontal cross bar's aperture. Here, the cap is lowered such that it is below the upper edge of the vertical ribs and, thus, the hex shaped hole is provided to allow and facilitate the dentist's vertical adjustment of the same;

FIG. 14 is a top plan perspective view of the bottom or lower tray, with palatal cap and its screw removed to show the details of the cross bar and it's three short vertical ribs;

FIG. 15 is a front perspective view of the present invention with no teeth yet secured to the vertical ribs of the lower tray, but showing the placement of the palatal arch, on the screw which is threaded into the cross bar of the lower tray;

FIG. 16 is a partial perspective view of the screw with palatal cap and the locking nut, the vertical ribs of the lower tray as the same is presented for use with a custom (partially closed off) lower tray;

FIG. 17 is a front perspective view of the lower tray, with the palatal arch and its screw threaded through the aperture of the cross bar of the lower tray and shows the vertical ribs for accepting wax from the rear of the artificial teeth so that the same can present the patient and dentist with a visual look of the proposed dentures;

FIG. 18 is a front perspective view of the lower tray, the palatal arch or cap of the screw held in the cross bar, and also shows the use of a front handle for the dentist to use in inserting and removing the device, and the use of an occlusal plate for alignment purposes, the vertical ribs not yet being used for holding artificial teeth;

FIG. 19 is another view similar to that of FIG. 18 but now shows a second embodiment of the occlusal plate with a rear connecting bar extending behind the threads of the screw of the palatal arch;

FIG. 20 is a view similar to that of FIGS. 18 and 19 and shows the use of impression shelves;

FIG. 21 is a view of the lower tray, palatal arch or cap of the screw in place within the aperture of the cross bar, also shows the vertical ribs for supporting artificial teeth and a handle for inserting and removing the same from the patient's mouth and a second embodiment, a cross hair-like device for facilitating alignment of the teeth to the patient's anatomy and ear lobes, lips, mouth and nostrils; and FIG. 22 is a front perspective view of the lower tray, the upper palatal arch held within the aperture of the cross bar via the screw threads of the arch, a locking nut, the head of the cap having a hex hole for facilitating upward and downward adjustment of the cap with respect to the lower tray, and also shows a handle and a set of vertical ribs for accepting the artificial teeth.

DETAILED DESCRIPTION OF THE DRAWINGS AND THE PREFERRED EMBODIMENTS OF THE PRESENT INVENTION

Description will now be given of the invention with reference to the attached FIGS. 1-10. It should be understood that these figures are exemplary in nature and in no way serve to limit the scope of the invention as the invention will be defined by the claims, as interpreted by the Courts in an issued US Patent.

Figure 5A:
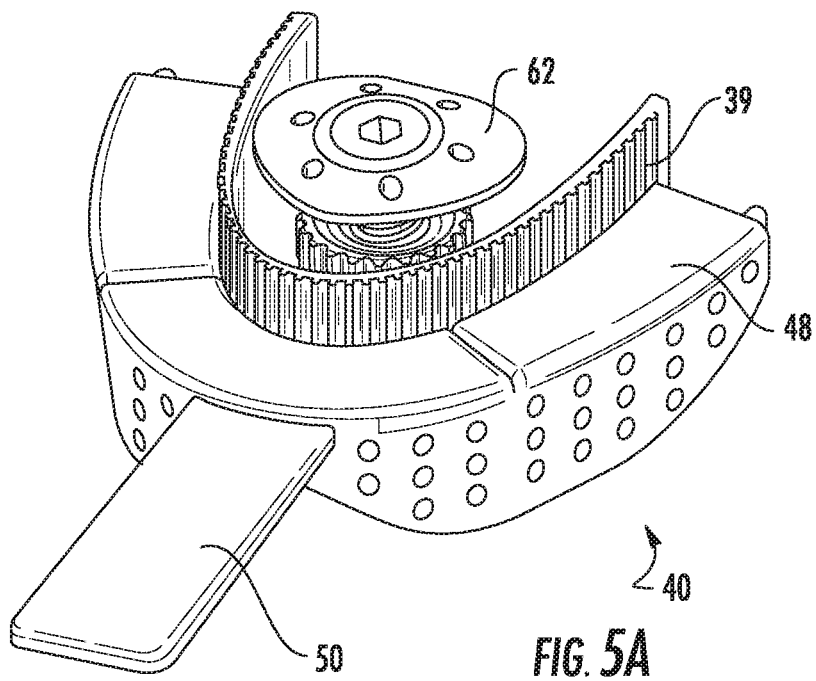
FIG. 5(a) is a front perspective view of the lower impression tray as seen in FIG. 2 with locking screw and partial palatal tray secured thereto for measurement of distance of occlusion in a patient's mouth and showing use of removable covers for the lower tray.

The present invention discloses the individual components, system, and method for preparing a set of dentures, preferably in a single visit, by using the patient's own mouth as the articulator for preparation and creation of the end-product, a set of dentures for a patient. To prepare a set of dentures according to the present invention, the dentist will first take or create an impression of the patient's lower jaw and gum ridge and upper jaw, palatal arch, gum ridge. Typically, for ease of illustration, these patients are edentulous so that the dental impression obtained from the inventive trays disclosed herein show no teeth but, rather, provide a negative or female mold of the internal gum lines and ridges and anatomical structure of the mouth, but basically, the gum lines. Of course, the present invention can be used where one or more teeth are present in the mouth of the patient (FIGS. 5a and 5 show a modified lower tray with covers for the part of the patient's mouth where teeth remain). In addition, the present invention can be used for other dental procedures, not requiring a complete set of dentures at all, but where a single tooth is required, a bridge, a partial denture, an implant, etc. Basically, the present invention is a simple and complete mechanism for using the patient's own mouth as the articulator for producing a positive image of the patient's mouth and orienting teeth with respect thereto for providing an attractive set of teeth, while providing inexpensive, disposable components for the same to reduce cost of the procedure for the patient and for providing accurate measurement and placement of the teeth/dentures in the patient's mouth.

Figure 1:
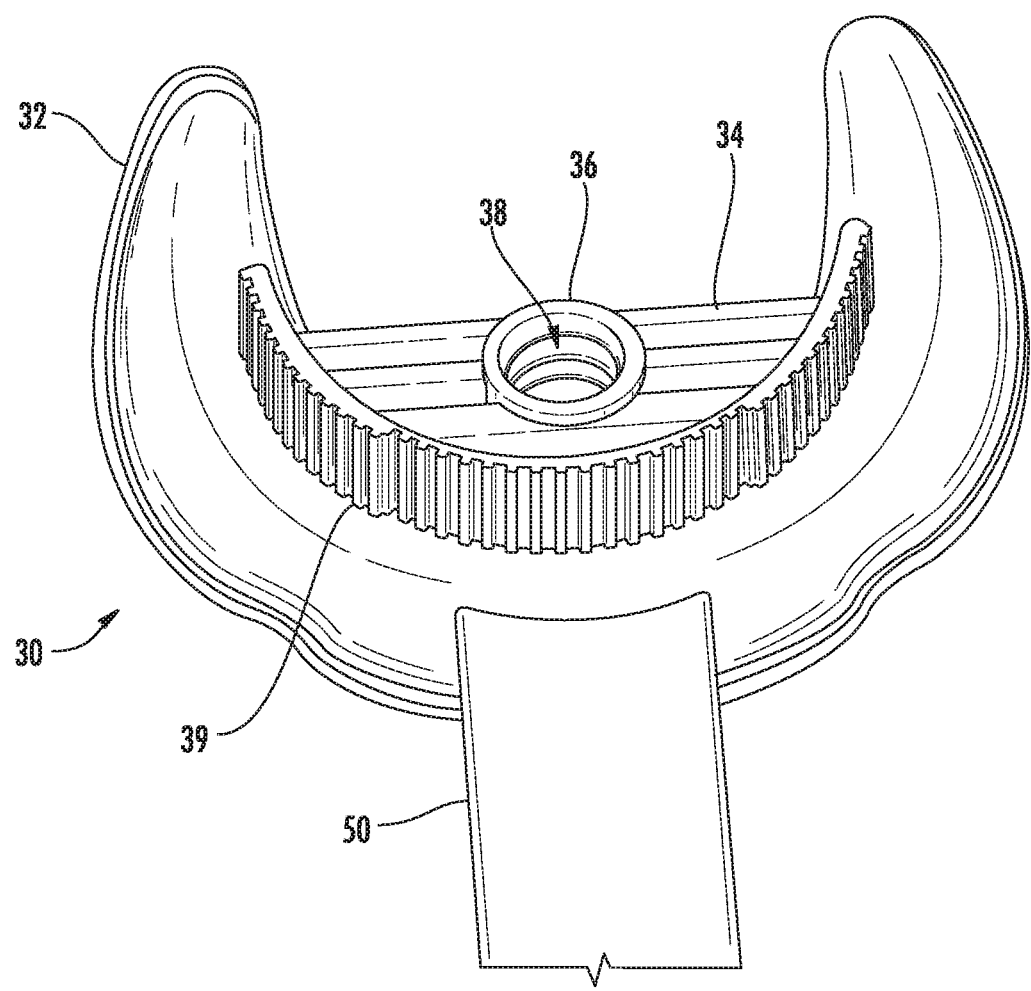
FIG. 1 is a front perspective view of a first embodiment of a new and one-time intended use, lower impression tray used in connection with the present invention for fully edentulous patients, with a handle (preferably removable) used for positioning the tray in relative location in the mouth for taking an impression.
Figure 1A:
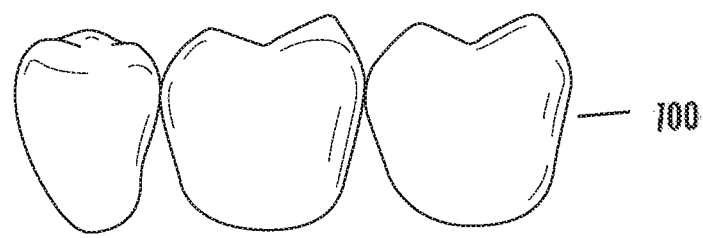
Figure 1B:
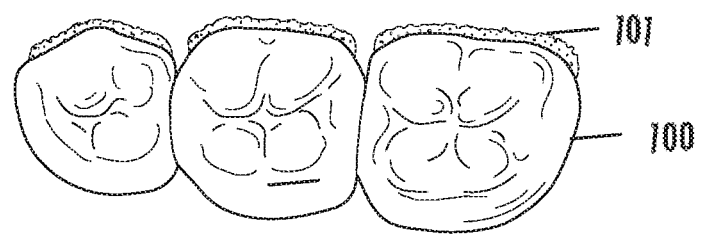
Figure 1C:
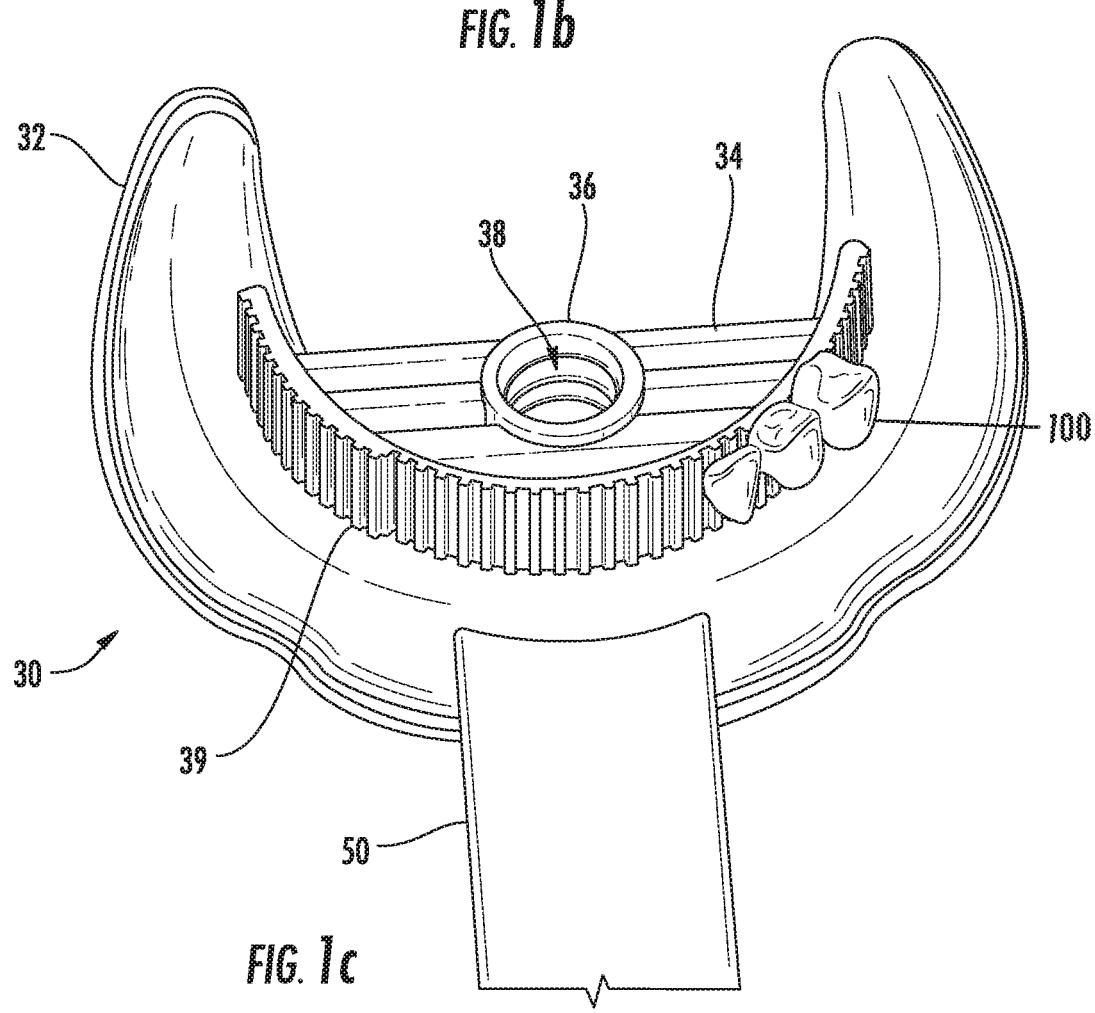
Figure 2:
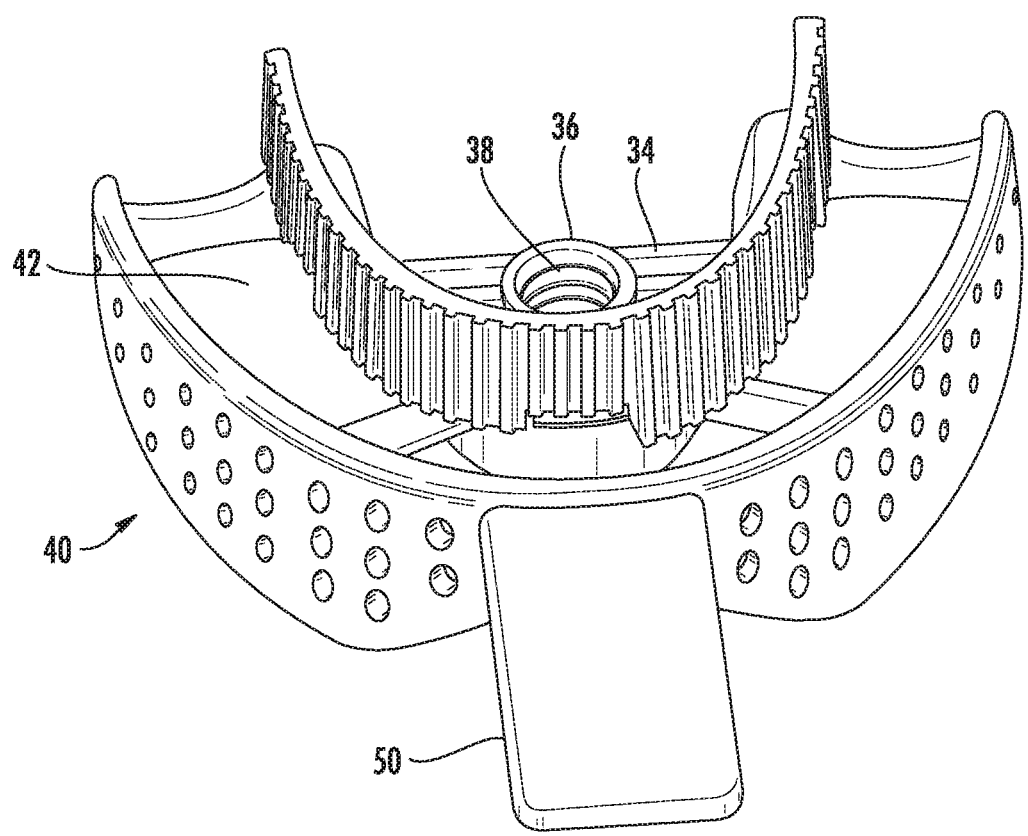
FIG. 2 is a front perspective view of a second embodiment of the new lower impression tray used in connection with the present invention for partially edentulous patients, with a handle used for positioning the tray in relative location in the mouth for taking an impression.

The impressions are taken of the upper and lower gum configurations by means of an upper and a lower tray which are configured to sit on the upper and lower gum lines, respectively. As can be seen in FIGS. 1 and 2, a lower tray 30 for fully edentulous patients and a lower tray 40 for partially edentulous patients are provided. Lower tray 30 comprises a trough 32 similar to a typical lower jaw or lower tooth dental impression tray (with a channel or trough in a curve to hold impression material and with upper rear and forward edges turned upwardly to hold the material therein during formation of the impression). Lower tray is provided with a plastic handle 50 which preferably extends forwardly and out the patient's mouth secured to the front edge of the lower tray 30, or preferably the handle can releasable secure to a small flange of the back of the lower tray by snapping onto the same. It is used for creating a first dental impression, a negative or female of the gum line of the patient's lower jaw or mouth/gums.

Lower tray 40, seen in FIG. 1, has the inverted trough sized and shaped to the patient's lower gum line. The handle is connected to the front for the dentist to grip the same. Extending across and inside of the sides of the trough is a connecting bridge or horizontal bar support 34. It is preferably comprised of parallel and spaced ribs 35. Preferably, the lower tray is made of inexpensive molded plastic, sturdy for support of impression material during formation and, yet, lightweight so that the dentist can manipulate the same and it is comfortable to the patient. The center of the horizontal bar support 34 is provided with a threaded aperture 36 with internal screw threads 38. Extending around and projecting outwardly from the mouth, on the top of the trough of the tray is a set of upwardly extending vertical ridges 29. These provide the back support for the artificial teeth when either or both are provided with wax, i.e., on the front of the ridges 29 or on the back of the artificial teeth. The wax will allow the teeth to be adjusted to the patient's mouth (until hardened by time or temperature or an light) and then hardened in place.

Lower tray 40 for use with partially edentulous patients comprises an open trough 42 surrounding the lower jaw line and gum lines to fit around and accommodate existing teeth and allow an impression made from a first tray to be placed therein for use with the artificial teeth when the patient has some tooth structure. Lower tray 40 also preferably has a handle 50 for placement of the lower tray 40 in the mouth of a patient. It, too, has a threaded central aperture 36 with screw threads 38 on a horizontal support bar 34. Also, it, too, has a set of vertically surrounding ridges 29; again, for support of the horizontal teeth when wax on the rear thereon is pressed against the ridges to frictionally support the same and, yet, allow minor adjustment or replacement, as desired, until the wax is cured or solidified.

Figure 3:
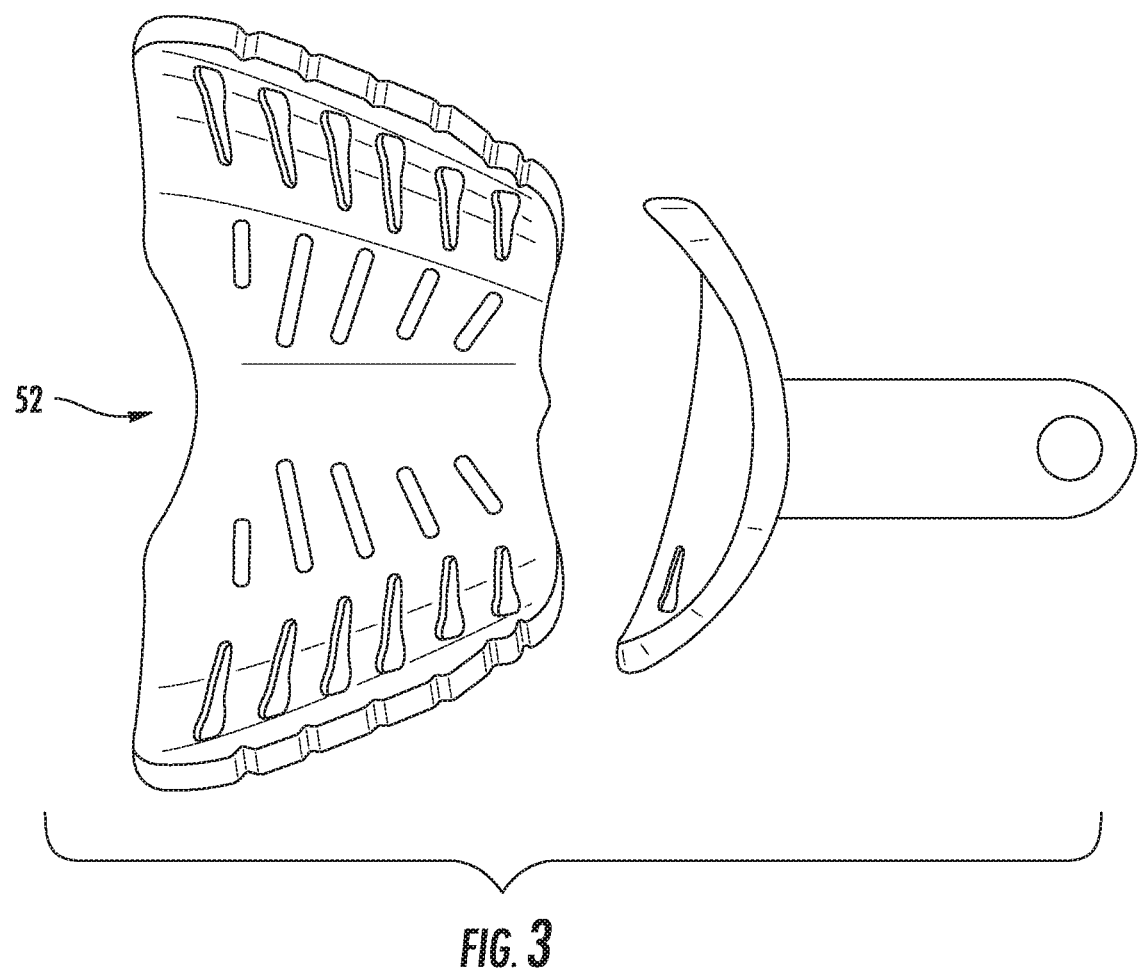
FIG. 3 is a top plan view of a new upper impression tray used in connection with the present invention for fully edentulous patients.

As can be seen in FIG. 3, an upper tray 52 can be used with the present invention system for forming an impression of the patient's upper palatal arch and/or mouth/gum line. The upper tray 52 can be substantially identical to the lower tray but sized and shaped to accommodate the roof or palatal arch of the mouth. It is used to create a dental impression of the patient's upper mouth or gum line for use in connection with formation of an upper set of dentures. While all three trays are available for use with the present invention, the system and method for making dentures disclosed by the present invention will be described using only lower tray 30 for fully endentulous patients for ease of reference. It is envisioned, however, that similar systems and methods can be utilized with lower tray 40 or upper tray 52, and this description and example should in no way limit the scope of the invention.

Figure 4A:
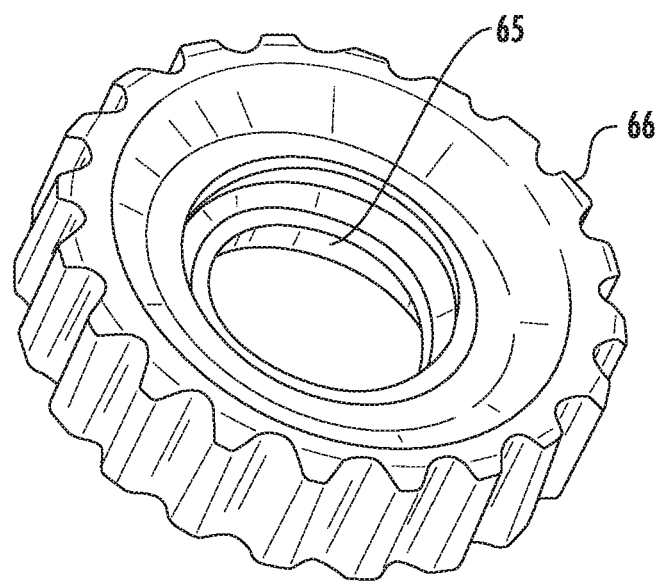
FIG. 4(a) is a front perspective view of the locking screw utilized with the trays of the present invention for measuring and maintaining the distance of occlusion in a patient's mouth.
Figure 4B:
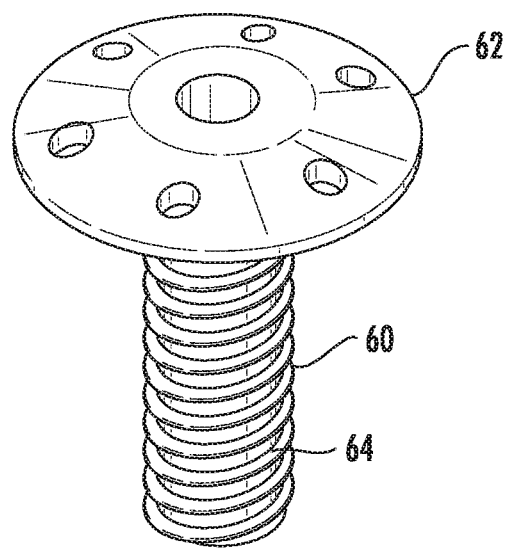
FIG. 4(b) is a front perspective view of a locking screw and partial palatal cap used to secure and preserve the distance between the partial palatal tray and the lower tray of the present invention for accurate measurement of the distance of occlusion.

As mentioned, lower tray 30 is preferably provided, within the center of its base, with a horizontal support bar 34 with an aperture 36 comprising internal screw threads 38. As seen in FIGS. 4(a) and 4(b), a screw 60 is provided, with a palatal tray or cap element 62 secured to its head. The screw 60 comprises external screw threads 64 which correspond and mate to the internal screw threads 38 of the aperture 36 in the horizontal support bar 24 of lower tray 30. When the screw 60 is inserted into the aperture 36, it can be rotated and lowered or raised with respect to the lower tray 30 until the palatal tray or cap element 62 a component of the screw 60 rests securely and comfortably on the bottom surface i.e., the palatal arch of the patient's mouth, accurately measuring the distance of occlusion, i.e., the distance between the upper roof of the mouth and the lower surface of the mouth, really being measured between the palatal arch and the lower tray's horizontal bar member. Thus, the distance defined by the interior of the patient's mouth will correspond to the distance between the bottom of lower tray 30 and the top or palatal tray 62, which rests comfortably against the palatal arch. The screw and the cap are also made of disposable plastic so that they, too, will be discarded after this patient's single use. Partial palatal tray 62 has a convex-shaped hill or roof section corresponding to the curvature of the inner surface or palatal arch of the mouth. A locking nut 66 (see FIG. 4*a*) is also provided, at the base of the screw threads of the screw. Locking nut 66 has internal screw threads 65 which match and mate with the external screw threads 64 of screw 60, and is adapted to be tightened down upon the horizontal bar support to secure the distance between the partial palatal arch or cap member and the horizontal support bar. The threads of the locking nut 66 interact and lock the screw 60 in place in aperture 36 once the locking nut 66 abuts the top of support horizontal bar 34.

When lower tray 30 is in the patient's mouth with the screw 60 and partial palatal tray or cap member 62 secured thereto, and the patient is told to "close" or "bite gently," the relative vertical spacing, locations of the partial palatal tray 62 and the horizontal support bar of the lower tray 30 will assume an orientation and spacing corresponding to that of the patient. Then, using the locking nut 66, the screw 60 can be held in place to configure the exact distance of occlusion in the patient's mouth. This is an important and significant step in the making of the dentures, using the components disclosed herein and the process described herein.

AS shown in FIG. 5*a*, a top plate 62 includes a male threaded shaft 64. A jam nut 66 surrounds and mates with the threads of the threads of the top plate. The jam nut locks the position of the top plate. The top plate threads into the bottom tray through the threaded aperture 36 located on the ribbed cross bar. To maximize the stability of the top plate, the following was considered:

The diameter of the threads was relatively large, which increased the left to right distance in between opposing threads, meaning that for a given amount of thread clearance the screw shaft would be able to tilt left and right to a smaller angle than if the threads 64 were smaller in diameter with the same slope.

The depth of thread engagement in the female threads 38 of the aperture 36 in the bottom tray were made large, too, to again provide more resistance to tipping of the screw within the aperture.

The jam nut, 66 when used, removed the slope in the threads and centered the threaded post quite well.

The diameter of the threaded portion is large enough that it is cored out and actually takes on a tubular form. A solid screw of this same diameter would not lend itself well to injection molding which is more suited to plastic parts with a uniform and relatively thin section. The tubular shape of the screw for the palatal arch allows for a more uniform and injection-molding friendly wall thickness while at the same time providing excellent rigidity of the shaft of the screw. This will allow the screw to better resist bending or flexing when subject to loads resulting from the patient biting down on the device.

In an alternate embodiment of the invention, the palatal arch, attached to the top of the screw threads, is provided with a central located hex hole to allow the dentist to turn and adjust the height of the arch with respect to the surrounding ribs, especially if the arch is screwed down so that it is below the surface of the top of the ribs. The bottom of the male thread of the device can be easily trimmed by the dentist, as needed (it is made of plastic) to avoid crowding of the tongue. In the embodiment of the device with the hex hole in the center of the cap of the device, the jam nut may not be present, allowing the entire cap to be lowered beneath that of the top edge of the ribs.

The crossbar 34, extending between the inside edges of the lower mouth tray has been designed as three lateral ribs (see FIG. 1). The cross bar consists of a horizontal plate with three short vertical ribs. The ribs help stiffen the crossbar which is considered important because there is a downward load coming from the palate and transferred through the top plate screw member and into the center of the cross bar. An opposing force originates from the lower gums and presses up on the impression tray and thereby upwards on the ends of the crossbar. As a result, the ends of the crossbar are pushed upwardly and the center is pushed relatively downwardly. If the crossbar were not stiffened by the vertical ribbing, there will be more than an acceptably allowable amount of deflection as the patient bites down on the device. When the device is then removed from the patient, such a weaker cross bar would resiliently return to its original shape and lift the top plate higher relative to the lower impression. This would result in the actual patient jaw angle not being accurately recorded by the device (a result sought to be avoided, of course) which would result in problems getting teeth properly located in the lab. Thus, the cross rib is necessarily strengthened and, yet, with minimum material for cost and manufacturing efficiency. The short vertical ribs are thus important.

Figure 7:
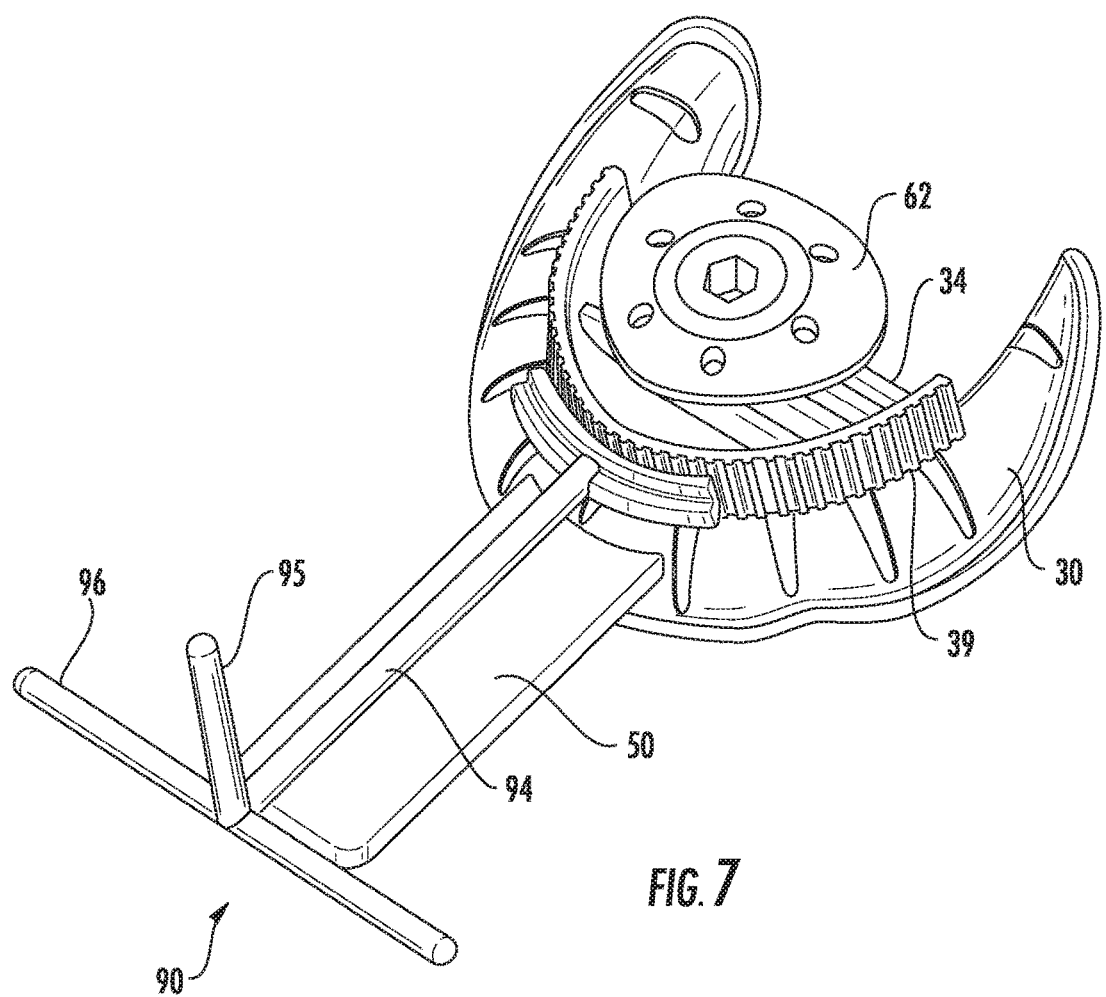
FIG. 7 is a front perspective view of the lower impression tray as seen in FIG. 6 with locking screw and palatal tray secured thereto and with teeth orientation level device for proper orientation and location of the tray within the mouth of the patient.
Figure 8:
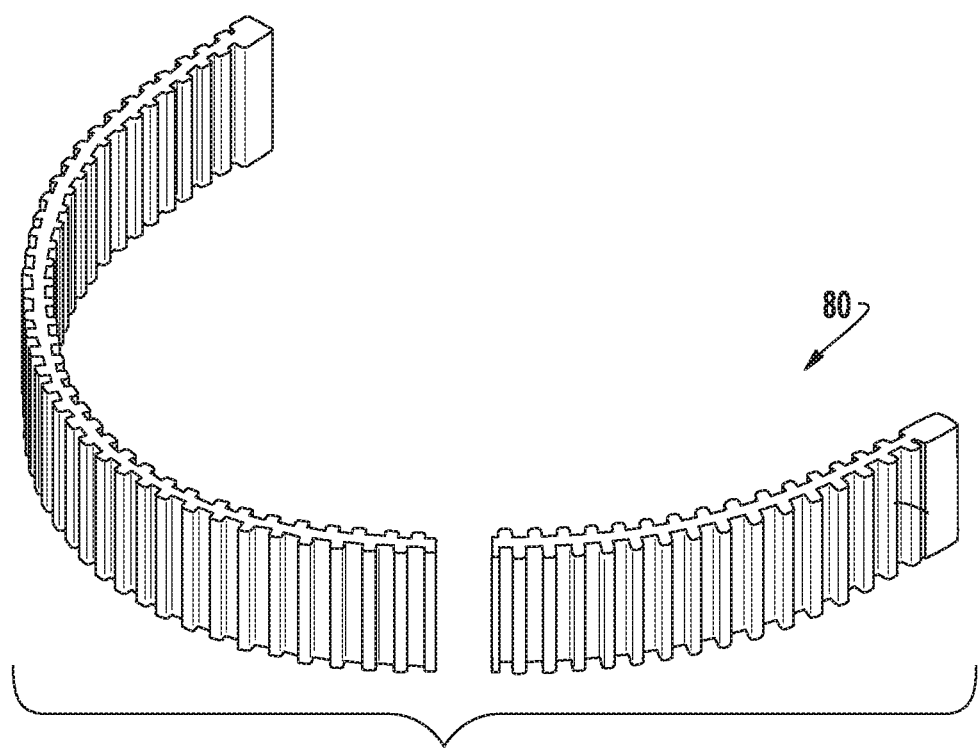
FIG. 8 is a side perspective view of a set of waxy ridged teeth holders of the present invention which are vertically ridged and can be secured to the rear of the artificial teeth so that the same position artificial teeth to the ridges of the trays of the present invention by wax on the back of the teeth being held to the ridges.
Figure 9:
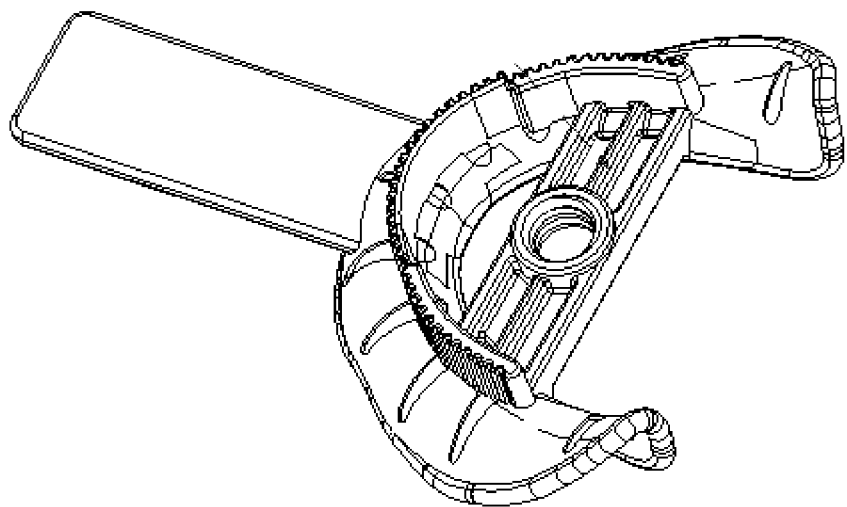
FIG. 9 is a front perspective view of the cross bar of the lower tray, with a threaded aperture for the partial palatal screw and the upwardly extending, semi-circular-like ridges.
Figure 10:
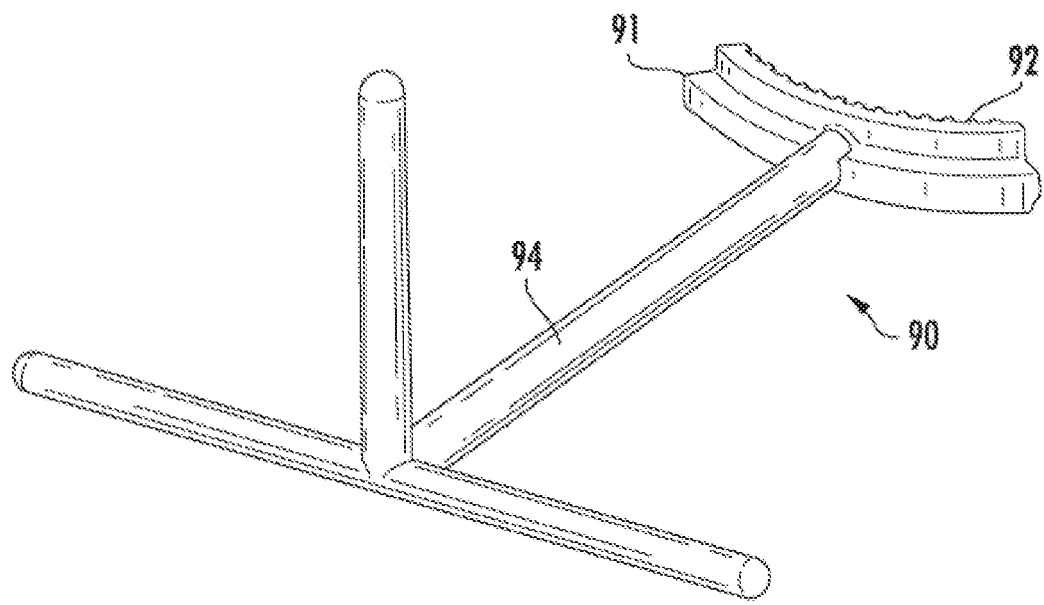
FIG. 10 is a front perspective view of the teeth orientation level of the present invention.

FIG. 7 shows the device with no teeth assembly and, yet, with the cap of the screw in place within the aperture of the cross bar. A device is there shown for helping the dentist orient the device by use of the patient's ear lobes, nose, mouth, etc. Alternatively, an occlusal plate member could be secured to the front of the vertical ribs which plate would extend, about the patient's mouth, in between his/her lips, for visual confirmation of the positioning by the dentist. In an alternative embodiment the occlusal plane could have a rear connecting bar, extending behind and between the inside of the occlusal plane towards the rear of the mouth for added stability. The device shown in FIG. 7 shows the device without any teeth yet secured to the vertical ribs but shows the sue of a cross hair handle device for facilitating orientation by the dentist. This cross hair device is shown in FIG. 10. As can be appreciated by a review of FIGS. 8 and 9, the tray is provided with a set of vertical ribs which are adapted to accept, secure and hold the rear of the teeth selectively attached thereto, during the orientation, selection of teeth for the patient. The vertical ribs can accept wax and thus frictionally will secure the rear of the artificial teeth as they are placed thereon by the dentist for color, size, orientation, etc.

In alternate embodiments of the invention, the tray of FIG. 2 is used. It is adapted to accept one or more cover pieces (corresponding to the locations of the patient's mouth and gums where teeth are still present). The covers are intended to be "snap-on" over areas or sections of the base tray, extending arc-like, and between the outside edge of the tray and the inside edge, where the vertical ribs are provided. This can be seen in FIG. 2 (although partial covers are not shown there). This version will accommodate those patients which are not fully edentulous but, rather, those with some teeth. So, then, provision must be made for gaps in the impression tray, corresponding to the presence of the patient's teeth. Every other aspect of the device and system is maintained as with the version of the same meant for edentulous patients (see FIG. 1). The function of providing selected gaps in the impression tray is accomplished by the use of up to three snap on covers which attach via small tabs and hooks to the outside of the tray (see FIG. 2) and the inside curved wall matching the curvature of the outside of the tray. A rib 11 is provided to the underside of the tabs to oppose the hook and prevent the tab from releasing (see FIGS. 11a, 11b, 11c and 11d) showing the tray with and without covers as well as a cross section of the device with covers (FIG. 11d) taken along lines B-B of FIG. 11c.

Artificial acrylic or porcelain teeth, set in wax in related sets (or single teeth) are provided, in accordance with the present invention. Various colors, shapes, sizes, are contemplated to be available to the dentist for purchase and selection with individual patients. The artificial teeth are preferably acrylic and preferably will be the actual teeth provided to the patient by the present invention, preferably in a set of complete acrylic gums and dentures. The teeth are provided in one or two waxes, the function of which will be described and reference is made to my prior US Patent application, incorporated by reference, U.S. Ser. No. 13/905,642 filed May 30, 2013, to which priority is claimed. A set of teeth is preferably a partial set of uppers or lowers. The teeth will be provided to the dentist and he will select the sets which most properly correspond to the type of teeth to be fitted, the color, shape and size, too. So, a dental office may have many sets of available artificial teeth to be used with the lower and upper trays herewith described.

According to the present invention, a front integrated set, for example, of six upper or six lower teeth are provided; a set of four right upper or four right lower teeth are provided, and a set of four left upper or four left lower teeth are also provided. This will provide, if required, a complete set of new dentures to the patient, comprising 14 upper teeth and 14 lower teeth. Each set of acrylic teeth is provided with a wax-like gum to hold adjacent teeth together in a set.

The sets of teeth can be provided with dental wax on their rear surface and then secured to the vertical ridges 39 for secure positioning of the same. The teeth holders 80 (see FIG. 8) can be press fit and secured to the vertical ridges 39 or the rear of the teeth are provided with wax which will allow the tooth/teeth in sets to be secured to the vertical wall 31 with the ridges secured to the top of the lower tray, at the rear edge of the trough. The teeth holders 80 can then be press fit to the ridges 29 and the wax of either the teeth holders 80 or the rear of the teeth holds the teeth to the lower tray. The teeth can be adjusted, moved, replace, until the dentist and patient are pleased with the result and then the wax cured or hardened. The rear of the sets of teeth can be alternatively provided with wax for holding the same either directly to the ridges 29 or to the teeth holders 80. The rear of the teeth holder arc 80 can be provided, too, with ridges which serve to mate and frictionally secure the same to the vertical ridges 29.

Prior to addition of the teeth holders 80, a teeth orientation level 90, as seen in FIG. 10, can be utilized. Teeth orientation level 90 is comprised of an arc end 91 with vertical ridges 92 on one end 91 thereof which correspond to the outwardly directed external ridges 29 of the lower tray 30, and can be placed thereon for a visual determination by the dentist of proper angle and distance of the lower tray 30 in the mouth of the patient. This can be seen in FIG. 7. Teeth orientation level 90 comprises a horizontally and out of the mouth extending rod 94 which extends outwardly from arced end 91 and ends at a point where a short rod 95 extends vertically therefrom and where a short rod 96 extends horizontally and across the lips of the patient, i.e., to create a 90 degree angle with the vertical rod 95. This level 90 allows a dentist to visually measure the angle of the lower tray 30 within the patient's mouth to ensure that the same is aligned with the patient's nose, lips, ears, and ala tragus. If it is not, screw 60 can be adjusted to alter the height and angle of the tray in the mouth and/or the teeth can be suitably adjusted.

The occlusal plane or level 90 has an interior arc 92 which abuts the outside of the vertical ridges 29 and an exterior to the mouth set of perpendicular rods (95 and 96) which facilitate the dentist's review of the placement of the teeth vis a vis the patient's head, ears, nose ala tragus, etc.

Now the dentures are to be formed, comprising the actual sets of teeth made of acrylic or porcelain with artificial or acrylic gums and a roof segment, also preferably formed of acrylic. In this connection, a conventionally available mechanical articulator can be used, or the teeth configurations can be sent to a lab for creation of the final product. Conventionally available impression trays are available and can be used for pouring of the positives of the impressions from dental stone. The dental stone fills in the gaps of the impressions, thereby creating a positive impression of the patient's mouth, the lower gums and the upper gums and including the roof, as it will form around the negative impression made by the impressions of the patient's mouth, from a complete upper tray and lower tray. The stone models will correspond precisely to the patient's mouth, with one stone model matching the curvature and shape of the upper mouth, gums and palatal or partial palatal roof, and one stone model matching that of the lower gum line of the patient's mouth. The upper and lower custom trays are formed from the stone models of the negative impressions first formed from the upper tray and the lower tray. Stated differently, the negative impressions first formed by the dentist are used for forming stone positives. Those, then, are used to form custom tray negatives.

FIG. 19 of the invention shown in my co-pending application Ser. No. 13/905,642 filed May 30, 2013, to which priority is claimed and which is incorporated by reference, shows the positive stone model impressions first formed by the negative impressions formed in the upper and lower trays. These are made from conventional dental stone and molding trays. They are used to form the custom trays 120 and 122 (not shown herein). Dental stone models 140 and 142 correspond to the positive replicas of the endentulous patient's mouth produced from the negative impressions of the trays. These dental stone molds correspond to the structure, shape, size and individuality of the patient's mouth.

After the stone models are complete, the custom trays or impressions are made from the stone models, respectively. Light-curable sheets of wax-like material can be placed over the upper and lower stone models and manually pushed and maneuvered into place along the positive impression portions of the stone models to form a thin, wax, custom negative impression tray of the top and bottom of the patient's mouth. Then, after pressing the sheets into the curves and crevices, and forms of the stone models, the sheets are cured to preserve their shape and form custom trays. When cured with light, the custom trays will set in place and form negatives of the patient's mouth which will fit perfectly onto the positives of the stone models.

Figures of my prior application Ser. No. 13/905,642 filed May 30, 2013, to which priority is claimed and which is incorporated by reference, shows the custom trays formed by the use of upper tray and a lower tray 30 which are used to form negative impressions and then stone models. From here, custom trays are made. These are made by use of lower tray 30 and upper tray 52.

Figure 5B:
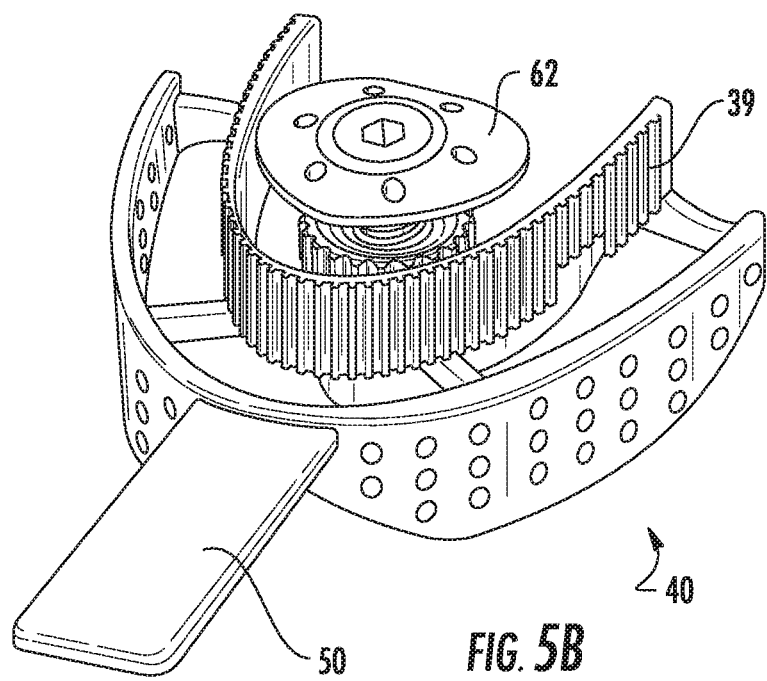
FIG. 5(b) is a front perspective view of the lower impression tray as seen in FIG. 5(a) with releasably securable covers removed for protection of existing teeth of the patient and for being used within the mouth of a partially edentulous patient.
Figure 6:
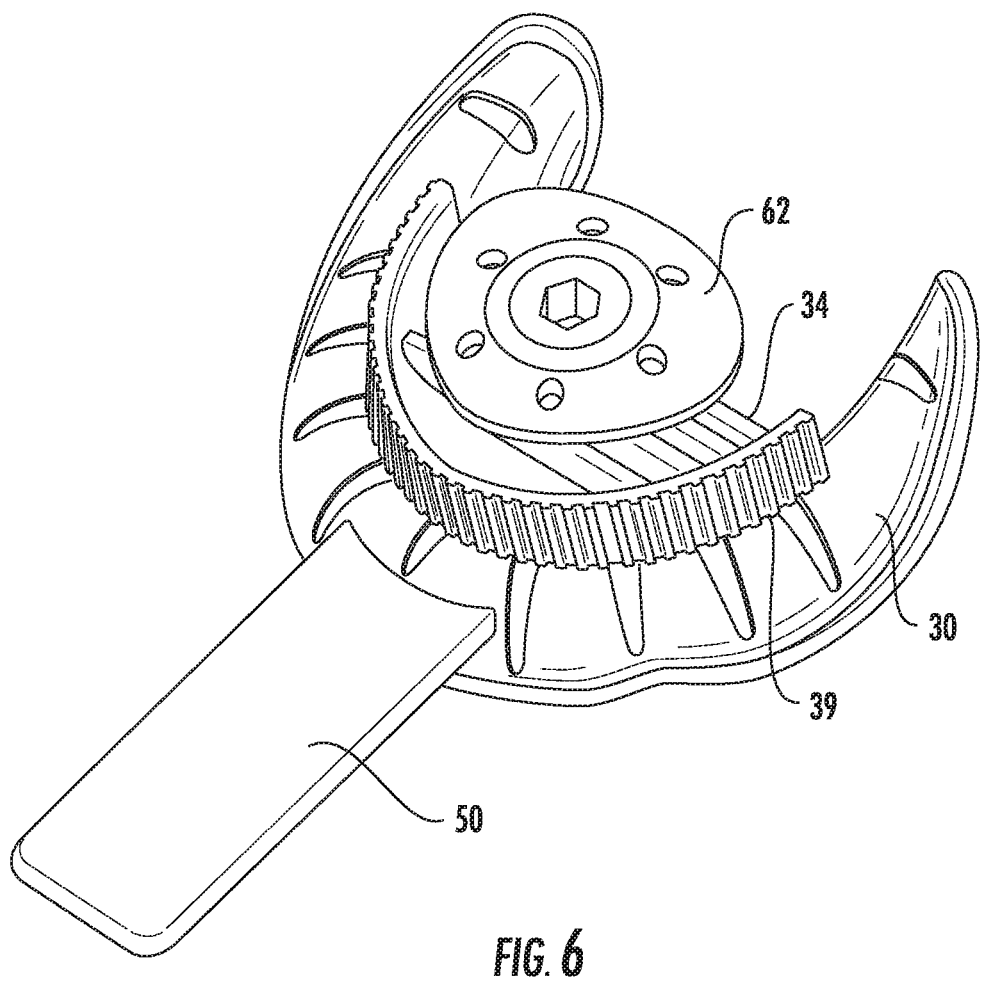
FIG. 6 is a front perspective view of the lower impression tray as seen in FIG. 1 with locking screw and partial palatal tray secured thereto for measurement of distance of occlusion in a patient's mouth.

According to the preferred use of my invention, lower tray 30 is preferably shaped to fit the curvature of the lower gums, generically, so that when filled with dental impression material it can be placed down onto the gum-line of a person who is edentulous and the impression material will mold and cure to its exact configuration. Lower tray 30 will be provided with impression material which is preferably made of a flexible, formable material, capable of being shaped in the exact configuration of the gum line. Once in place, lower tray 30 can be placed (using the convenient handle) down onto the gums, and the impression material will mold into the exact curvature and formation of the lower gum line, and will cure and harden in that configuration. A lower tray 40 can be used for partially edentulous patients, as seen in FIG. 5(*a*) and covers 48 can be snapped onto the lower tray 40 to cover the spacing 42 where there are existing teeth, as can be seen in FIGS. 2, 5*a* and 5*b*. An upper tray 52 can be used which is quite similar to that of the lower tray for taking the impression of the upper gums and roof of the mouth of the patient. The upper tray, too, will generally match the upper gum line and roof. It, too, will be first filled with soft impression material, then lifted into the patient's mouth and placed along the upper gums and the roof of the mouth, and, as the impression material molds and cures, provides an accurate mold of the upper region of the mouth. Partial palatal tray or screw cap 62 is designed to replace the upper impression formed by the upper tray 52 as it is believed that use of a full lower tray, an impression therein, and a full upper tray with impression may just be too much for a patient to comfortably hold in position during the subsequent steps. Thus, partial palatal tray 62 has been provided, releasably secured to lower tray 30 by means of screw 60, to allow the lower tray and the palatal tray to fit within and thus the mouth of the patient to serve as the dental articulator. According to the preferred embodiment of the present invention, the partial palatal tray or screw cap 62 substitutes for the full upper tray 52 but, of course, the upper tray with impression material therein can be used. According to the preferred embodiment of the present invention, the upper tray 52 and the formed impression of the upper gums and the roof of the mouth is placed aside until needed for use, later (in creating a stone mold of the upper).

Once palatal tray 62 is desirably properly located and the screw 60 has been locked into place with the locking nut 66 on the lower tray 30, a cured dental impression of the lower gums can be in place, with the dentist checking for proper bite, etc. The use of the occlusal plane or level device is also helpful to determine proper positioning.

As more fully described above, each tray is preferably provided with a snap on and off, removably coupled handle 50, capable of attaching to the tray for controlling and directing the tray into the desired location in the mouth. The handle allows a dentist to properly position the tray(s) into the mouth along the upper and lower gums and hold them in place so that the impression material can harden. Of course, the adjustment of the artificial teeth, capable of being easily performed because of the use of wax to secure the teeth to the ridges 29 of the trays, is facilitated by the use of the occlusal plane and all is accomplished according to the anatomy of the patient's mouth and standard and conventional dental principles.

Once adjustment is made and the trays locked into position, the dentist will start to assemble the units of teeth and attach the same to the trays. A complete set of dentures is preferably made using a plurality of sets of teeth which are preferably made of acrylic or even porcelain. These teeth, in color, shape, size, etc., are preferably the actual teeth which will be provided in the end product, a complete set of dentures. These individual acrylic teeth are currently commercially available but have never been used in the manner currently contemplated. A complete set of teeth is now possible, with a single sitting of the patient, with proper spacing, angling, and positioning for final creation of the dentures, since the use of the patient's own mouth as the articulator helps eliminate errors in the positioning and curvature of the dentures. Now, a complete set of final dentures secured to the trays are provided which can be formed, outside of the patient's mouth, into a set of dentures, using the impressions of the gum lines first formed by the upper tray and the lower tray.

As seen in FIG. 11, a standard dental articulat 19 of my prior filed U.S. patent application Ser. No. 13/905,642 filed May 30, 2013, to which priority is claimed and which is incorporated by reference, mechanical articulator can be used as a holding unit for the stone models, the custom trays, and the impression trays. Quick setting and first soft dental plaster can be placed on the flat bottom and top surfaces, respectively, of the lower and upper stone models and then they are placed onto the flat surface of the top plane and the flat surface of the bottom plane of the articulator. The lower stone model, with the lower tray in place thereon, and with the custom tray are thus placed onto the mechanical articulator. This will be held in place by the quick setting dental plaster. Similarly, the upper stone model and the upper custom tray are located in the mechanical articulator. The artificial teeth of the upper stone model and the lower stone model are made to properly set and mesh. The quick setting dental plaster will solidify.

The mechanical articulator thus holds a "dental sandwich" starting from the top to the bottom, as follows: the underneath or bottom portion of the top surface of the conventional articulator; originally soft but soon-to-harden dental plaster; secured thereto will be the flat surface of the upper stone model, with the positive of the stone model in the position as if replicating the patient's mouth; i.e., the set of stone gums and palatal roof, will be provided with the custom tray of the roof of the mouth and the upper gum line; then below it will be the partial palatal tray and screw secured to lower tray 30; which contains the custom tray of the lower gums; which then sits upon the positive of the gums of the lower mouth, formed on the stone model, (flat side of the stone model being faced down); which then has quick-to-harden dental plaster; sitting directly upon the top of the bottom flat surface of the conventional articulator. Quick setting dental plaster is used and poured on top of the upper stone model and beneath the lower stone model to fill in the gap between the top of the upper stone model and the mechanical articulator, and the bottom of the lower stone model and the mechanical articulator, thereby holding all pieces in place at a desired orientation for the patient's mouth. Dental plaster is used and poured below the lower stone model to fill in the gap between the bottom (flat) of the lower stone model and the conventional articulator. This serves to hold all components in place in the conventional mechanical articulator. If the configuration of the stone models, the upper and lower trays, and the custom trays are done accurately, a substantially perfect reconstruction of the mouth has been made and is set forth in the conventional mechanical articulator with the acrylic teeth shown as they will be displayed in a final set of dentures.

Once the custom trays are secured to the stone models, respectively, by use of dental plaster, commercially available baseplate dental wax can be heated up and manually attached to close the gap between the custom trays and the tops of the waxed teeth for the uppers and the bottom of the waxed teeth for the lowers. This dental base-plate wax will become malleable once heated, and is adapted to be inserted along any ridges or troughs in the custom trays. The combination of baseplate wax and custom trays and the wax of the teeth will create a mold of the gums of the patient so as to perfectly match that patient's mouth, and connect the teeth sets to the custom trays. This will provide a dentist with the correct anatomy, height and depth of the dentures with teeth properly positioned. The custom trays are the wax equivalent of the acrylic of the dentures. This step can be performed for both the lower and upper custom trays.

At this point, standard dental principles and procedures can be used to create the final set of dentures from the custom trays, the baseplate wax and the acrylic teeth. A set of upper and lower complete dentures will be formed with the teeth precisely positioned as they were in the trays.

The present invention presents a system, components and method for accurate creation of a set of dentures using the patient's mouth as the articulator, preferably using all inexpensive and disposable components, and preferably utilizing a process which can be completed in a single visit.

It will be understood by those of ordinary skill in the art that various changes may be made and equivalents may be substituted for elements without departing from the scope of the invention. In addition, many modifications may be made to adapt a particular feature or material to the teachings of the invention without departing from the scope thereof. Therefore, it is intended that the invention not be limited to the particular embodiments disclosed, but that the invention will include all embodiments falling within the scope of the claims.

What is claimed:

1. A dental tray system for making dentures comprising a palatal arch surface having a central screw member extending downwardly therefrom; a gum covering lower dental tray, said lower dental tray being generally in a U-shape corresponding to the general curvature of a mouth and gums of a patient, extending from one side of the mouth to the other, and thus defining a pair of opposed legs of the U-shape of the lower dental tray for creating a lower dental impression of a patient from conventional dental tray molding material, said lower dental tray defining an inverted trough for containing the conventional dental tray molding material and being non-metallic and disposable after intended single use and further comprising:

a suspended horizontal connecting bar extending between said two legs of said U-shape of said lower dental tray and having a central aperture with internal screw threads for accepting said central screw member of said palatal arch surface;

and an upwardly extending, arch-shaped back support surface extending around said lower dental tray and generally following the shape of said U-shape of said lower dental tray, from opposed leg to opposed leg, said back support surface extending above the top edge of said lower dental tray and being ribbed for mechanically accepting and holding the rear surface of one or more artificial teeth securable and temporarily adjustable thereto.

2. A dental tray system as claimed in claim 1 wherein said lower dental tray further comprises a removable handle extending centrally and forwardly of said trough.

3. A dental tray system as claimed in claim 1 wherein said central screw member is provided with a locking nut which is capable of bearing down and against said horizontal connecting bar to lock said central screw member in relative vertical position with respect to said lower dental tray.

4. A dental tray and denture making system comprising:

a one-time intended use and then disposable dental impression lower tray having an opposed set of legs forming a U-shape comprising an inverted trough for dental molding material, said legs and U-shape corresponding to the size and curvature of the mouth and the gums of a patient and a suspended horizontal support bar extending between the legs of said U-shape of said lower tray, said horizontal support bar having a central aperture with internal screw threads;

a palatal element having a central threaded and downwardly extending screw member defining a generally vertical axis for vertically adjustable and mating receipt in said internal screw threads of said central aperture; and an upwardly extending backing wall located generally extending around said inverted trough and above the top edge of said inverted trough, said backing wall also generally corresponding to the curvature of the mouth and gums of a patient and at least one artificial tooth with a rear holding element for engaging and holding said artificial tooth (teeth) against said upwardly extending wall.

5. A dental tray system as claimed in claim 4 wherein said lower tray is made of plastic.

6. A dental tray system as claimed in claim 4 further comprising a removable handle securable to and removable from the front of said lower tray.

7. A dental tray system as claimed in claim 4 wherein said screw member is further provided with a locking nut member for maintaining the relative vertical receipt of said palatal element above said horizontal support bar.

8. A dental tray system as claimed in claim 4 further comprising a visual facilitating leveling device selectively securable to said lower tray and having small rods projecting outwardly from the mouth of a patient having said lower tray installed in the patient's mouth, said small rods defining, at least two perpendicular axes to ensure the proper orientation of said lower tray with respect to the eyes, ears, nose and/or ala tragus of a patient.

* * * * *